(12) United States Patent
DeLuca et al.

(10) Patent No.: US 8,404,666 B2
(45) Date of Patent: *Mar. 26, 2013

(54) 2-SUBSTITUTED-1α,25-DIHYDROXY-19,26,27-TRINOR VITAMIN D ANALOGS AND USES THEREOF

(75) Inventors: Hector F. DeLuca, Deerfield, WI (US); Lori A. Plum, Arena, WI (US); Margaret Clagett-Dame, Deerfield, WI (US); Pawel Grzywacz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 176 days.

This patent is subject to a terminal disclaimer.

(21) Appl. No.: 11/697,434

(22) Filed: Apr. 6, 2007

(65) Prior Publication Data

US 2007/0238704 A1 Oct. 11, 2007

Related U.S. Application Data

(60) Provisional application No. 60/744,386, filed on Apr. 6, 2006.

(51) Int. Cl.
*A61K 31/59* (2006.01)
*C07C 401/00* (2006.01)

(52) U.S. Cl. ........................................ 514/167; 552/653
(58) Field of Classification Search .................. 514/167; 552/653

See application file for complete search history.

(56) References Cited

U.S. PATENT DOCUMENTS

| | | | |
|---|---|---|---|
| 4,188,345 A | 2/1980 | DeLuca et al. | |
| 4,411,833 A | 10/1983 | DeLuca et al. | |
| 4,666,634 A | 5/1987 | Miyamoto et al. | |
| 4,970,203 A | 11/1990 | DeLuca et al. | |
| 5,086,191 A | 2/1992 | DeLuca et al. | |
| 5,536,713 A | 7/1996 | Deluca et al. | |
| 5,585,369 A | 12/1996 | DeLuca et al. | |
| 5,843,928 A * | 12/1998 | Deluca et al. | 514/167 |
| 5,880,114 A | 3/1999 | DeLuca et al. | |
| 5,936,133 A | 8/1999 | DeLuca et al. | |
| 5,945,410 A | 8/1999 | DeLuca et al. | |
| 6,127,559 A | 10/2000 | DeLuca et al. | |
| 6,277,837 B1 | 8/2001 | DeLuca et al. | |
| 6,291,444 B1 | 9/2001 | DeLuca et al. | |
| 6,306,844 B1 | 10/2001 | DeLuca et al. | |
| 6,382,071 B1 | 5/2002 | Bertani et al. | |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 6,844,330 B2 | 1/2005 | DeLuca et al. | |
| 6,844,331 B2 | 1/2005 | DeLuca et al. | |
| 6,844,332 B2 | 1/2005 | DeLuca et al. | |
| 6,844,457 B2 | 1/2005 | DeLuca et al. | |
| 6,846,811 B2 | 1/2005 | DeLuca et al. | |
| 6,887,860 B2 | 5/2005 | DeLuca et al. | |
| 6,992,074 B2 | 1/2006 | DeLuca et al. | |
| 7,053,075 B2 | 5/2006 | DeLuca et al. | |
| 7,241,749 B2 | 7/2007 | DeLuca et al. | |
| 7,241,909 B2 * | 7/2007 | DeLuca et al. | 552/653 |
| 7,242,749 B2 * | 7/2007 | Hsieh et al. | 378/150 |
| 7,528,122 B2 * | 5/2009 | DeLuca et al. | 514/167 |
| 7,648,973 B2 * | 1/2010 | DeLuca et al. | 514/167 |
| 7,704,981 B2 * | 4/2010 | DeLuca et al. | 514/167 |
| 7,803,789 B2 * | 9/2010 | Deluca et al. | 514/167 |
| 2003/0158157 A1 | 8/2003 | DeLuca et al. | |
| 2004/0229851 A1 | 11/2004 | DeLuca et al. | |
| 2005/0119242 A1 | 6/2005 | DeLuca et al. | |
| 2007/0191316 A1 | 8/2007 | DeLuca et al. | |
| 2007/0191317 A1 | 8/2007 | DeLuca et al. | |
| 2007/0238702 A1 | 10/2007 | DeLuca et al. | |

FOREIGN PATENT DOCUMENTS

| | | |
|---|---|---|
| WO | WO 98/41501 | 9/1998 |
| WO | WO 02/05823 | 1/2002 |
| WO | WO 02/058707 | 8/2002 |
| WO | 02/094247 | 11/2002 |
| WO | 2004/080922 | 9/2004 |
| WO | 2005/018648 | 3/2005 |
| WO | 2005/051323 | 6/2005 |
| WO | WO 2006/119309 | 11/2006 |

OTHER PUBLICATIONS

Baggiolini et al., "Stereocontrolled Total Synthesis of 1α,25-Dihydroxycholecalciferol and 1α,25-Dihydroxyergocalciferol," Journal of Organic Chemistry, 51, pp. 3098-3108, (1986).

Collins et al, "Normal Functional Characteristics of Cultured Human Promyelocytic Leukemia Cells (HL-60) After Inducation of Differ- Competitive VDR Binding

■ $1,25(OH)_2D_3$
× RA-7

$K_i$: $1,25(OH)_2D_3 = 1 \times 10^{-10}$ M
RA-7 = $1 \times 10^{-9}$ M entiation by Dimethylsulfoxide," The Journal of Experimental Medicine, vol. 149, pp. 969-974, (1979).

Corey et al, "Computer-Assisted Synthetic Analysis. A Rapid Computer Method for the Semiquantitative Assignment of Conformation of Six-Membered Ring Systems. 1. Derivation of a Preliminary Conformational Description of the Six-Membered Ring," The Journal of Organic Chemistry, vol. 45, No. 5, pp. 757-764, (1980).

Daniewski et al, "A Novel Silylcopper Catalyst for the Reductive Bromination of Hajos Dione. Improved Preparation of a CD Synthon for the Synthesis of Vitamin D," Journal of Organic Chemistry, vol. 66 No. 2, pp. 626-628, (2001).

Fall et al, "Vitamin D Heterocyclic Analogues. Part 1: A Stereoselective Route to CD Systems with Pyrazole Rings in their Side Chains," Tetrahedron Letters 43, pp. 1433-1436, (2002).

Glebocka et al, "New Derivative of $1\alpha,25$-Dihydroxy-19-Norvitamin $D_3$ with 3'-Alkoxypropylidene Moiety at C-2: Synthesis, Biological Activity and Conformational Analysis," Journal of Steroid Biochemistry & Molecular Biology, vols. 89-90, pp. 25-30, (2004).

Granja et al, "Studies on the Opening of Dioxanone and Acetal Templates and Application to the Synthesis of $1\alpha,25$-Dihydroxyvitamin $D_2$," Journal of Organic Chemistry, vol. 58, pp. 124-131, (1993).

Hanessian et al, "Total Synthesis of (−)-Reserpine Using the Chiron Approach," Journal of Organic Chemistry, vol. 62, pp. 465-473, (1997).

Inhoffen et al, "Studies in the Vitamin D Series, XXI: Hydrindane Compounds from Vitamin $D_3$," Chemische Berichte, vol. 90, pp. 664-673, (1957).

Lythgoe et al, "Calciferol and its Relatives. Part22. A Direct Total Synthesis of Vitamin $D_2$ and Vitamin $D_3$," J. Chem. Soc. Perkin Trans. 1, p. 590, (1978).

Lythgoe, "Synthetic Approaches to Vitamin D and its Relatives," Chem. Soc. Rev. 9, p. 449, (1983).

Mincione et al, "Improved Conversion of Vitamin $D_2$ into the Windaus Ketone and its Regioselective Hydroxylation via Organoboranes at $C_{26}$," Synthetic Communications, vol. 19 Nos. 5-6, pp. 723-735, (1989).

Miyamoto et al, "Synthetic Studies of Vitamin D Analogues. XIV. Synthesis and Calcium Regulating Activity of Vitamin $D_3$ Analogues Bearing a Hydroxyalkoxy Group at the $2\beta$-Position," Chem. Pharm. Bull., vol. 41 No. 6, pp. 1111-1113, (1993).

Nishii et al, "The Development of Vitamin $D_3$ Analogues for the Treatment of Osteoporosis," Osteoporosis Int., Suppl. 1, pp. S190-S193, (1993).

Okamura et al, "Vitamin D: Concerning the Relationship Between Molecular Topology and Biological Function," Proc. Nat. Acad. Sci. U.S.A., vol. 71 No. 10, pp. 4194-4197 (1974).

Okano et al, "Regulatory Activities of $2\beta$-(3-Hydroxypropoxy)-$1\alpha,25$-Dihydroxy-Vitamin $D_3$, a Novel Synthetic Vitamin $D_3$ Derivative, on Calcium Metabolism," Biochemical and Biophysical Research Communications, vol. 163 No. 3, pp. 1444-1449, (1989).

Ono et al, "Efficient Synthesis of 2-Modified $1\alpha,25$-Dihydroxy-19-norvitamin $D_3$ with Julia Olefination: High Potency in Induction of Differentiation on HL-60 Cells," Journal of Organic Chemistry, vol. 68, pp. 7407-7415, (2003).

Ostrem et al, "24- and 26-homo-1,25-dihydroxyvitamin $D_3$: Preferential activity in inducing differentiation of human leukemia cells HL-60 in vitro," Proc. Natl. Acad. Sci. USA, vol. 84, pp. 2610-2614, (1987).

Perlman et al, "$1\alpha,25$-Dihydroxy-19-Nor-Vitamin $D_3$. A Novel Vitamin D-Related Compound with Potential Therapeutic Activity," Tetrahedron Letters, vol. 31 No. 13, pp. 1823-1824, (1990).

Perlman et al, "Novel Synthesis of 19-Nor-Vitamin D Compounds," Tetrahedron Letters, vol. 32 No. 52, pp. 7663-7666, (1991).

Peterson et al, "Studies of the Ketone Obtained from the Ozonolysis of Vitamin D. Molecular Mechanics Calculations for It and Related Hydrindanones," Journal of Organic Chemistry, vol. 51 No. 11, pp. 1948-1954 (1986).

Plum et al, "Biologically Active Noncalcemic Analogs of $1\alpha,25$-Dihydroxyvitamin D with an Abbreviated Side Chain Containing No Hydroxyl," PNAS, vol. 101 No. 18, pp. 6900-6904, (2004).

Posner et al, "Stereocontrolled Total Synthesis of Calcitriol Derivatives: 1,25-Dihydroxy-2-(4'-hydroxybutyl)vitamin $D_3$ Analogs of an Osteoporosis Drug," Journal of Organic Chemistry, vol. 59 No. 25, pp. 7855-7861, (1994).

Posner et al, "2-Fluoroalkyl A-Ring Analogs of 1,25-Dihydroxyvitamin $D_3$. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).

Rochel et al, "The Crystal Structure of the Nuclear Receptor for Vitamin D Bound to Its Natural Ligand," Molecular Cell, vol. 5, pp. 173-179, (2000).

Sardina et al, "Studies on the Synthesis of Side-Chain Hydroxylated Metabolites of Vitamin D. 2. Stereocontrolled Synthesis of 25-Hydroxyvitamin $D_2$," J. Org. Chem., 51, pp. 1264-1269, (1986).

Sicinski et al, "New $1\alpha,25$-Dihydroxy-19-Norvitamin $D_3$ Compounds of High Biological Activity: Synthesis and Biological Evaluation of 2-Hydroxymethyl, 2-Methyl, and 2-Methylene Analogues," Journal of Medical Chemistry, 41, pp. 4662-4674, (1998).

Sicinski et al, "New Highly Calcemic $1\alpha,25$-Dihydroxy-19-Norvitamin $D_3$ Compounds with Modified Side Chain: 26,27-Dihomo- and 26,27-Dimethylene Analogs in 20S-Series," Steroids, vol. 67, pp. 247-256, (2002).

Sicinski et al, "2-Ethyl and 2-Ethylidene Analogues of $1\alpha,25$-Dihydroxy-19-Norvitamin D3: Synthesis, Conformational Analysis, Biological Activities, and Docking to the Modeled rVDR Ligand Binding Domain," Journal of Medical Chemistry, vol. 45, pp. 3366-3380, (2002).

Tocchini-Valentini et al, "Crystal Structures of the Vitamin D Receptor Complexed to Superagonist 20-epi Ligands," Proc. Natl. Acad. Sci. USA, vol. 98 No. 10, pp. 5491-5496, (2001).

Toh et al, "Studies on a Convergent Route to Side-Chain Analogues of Vitamin D: 25-Hydroxy-23-Oxavitamin $D_3$," J. Org. Chem., 48, 1414, (1983).

Windaus et al, "The Constitution of Vitamin $D_2$ Part II," Annalen der Chemie, 524, pp. 295-299, (1936).

Yoshida et al, "Efficient and Convergent Coupling Route for the Short-step Synthesis of Enantiopure $2\alpha$- and $2\beta$-Alkylated $1\alpha,25$-Dihydroxy-19-norvitamin $D_3$ Analogues," Synlett, No. 8, pp. 1175-1179, (2003).

* cited by examiner

*Primary Examiner* — Sabiha N Qazi

(74) *Attorney, Agent, or Firm* — Andrus, Sceales, Starke & Sawall, LLP

(57) ABSTRACT

Compounds of formula I, II or III are provided where $X_1$, $X_2$ and $X_3$ are independently selected from H and hydroxy protecting groups and $R_1$ and $R_2$ are independently selected from H or straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms; and $R_3$ is independently selected from straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms. Such compounds are used in preparing pharmaceutical compositions and are useful in treating a variety of biological conditions.

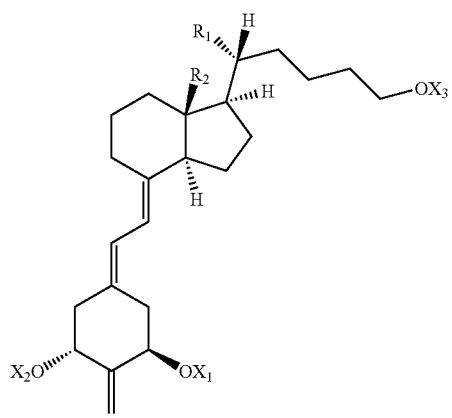
I
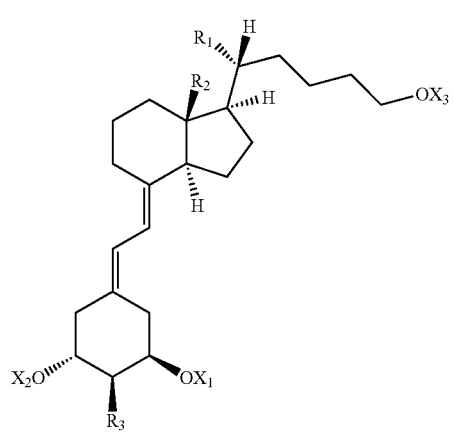
II
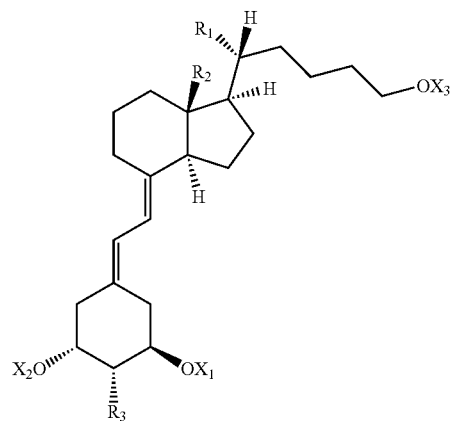
III
26 Claims, 5 Drawing Sheets

2-SUBSTITUTED-1α,25-DIHYDROXY-19,26,27-TRINOR VITAMIN D ANALOGS AND USES THEREOF

CROSS-REFERENCE TO RELATED APPLICATION

This application claims the benefit of U.S. Provisional application 60/744,386, filed Apr. 6, 2006, incorporated herein by reference in its entirety for all purposes.

FIELD OF THE INVENTION

This invention relates to vitamin D compounds, and more particularly to (20R)-2-methylene-19,26,27-trinor-1α,25-dihydroxycalciferol (RA-7), (20R)-2β-methyl-19,26,27-trinor-1,25-dihydroxycalciferol and (20R)-2β-methyl-19,26,27-trinor-1α,25-dihydroxycalciferol and to pharmaceutical formulations that include these compounds. The invention also relates to the use of (20R)-2-methylene-19,26,27-trinor-1α,25-dihydroxycalciferol (RA-7), (20R)-2α-methyl-19,26,27-trinor-1α,25-dihydroxycalciferol and (20R)-2β-methyl-19,26,27-trinor-1α,25-dihydroxycalciferol or salts thereof in the preparation of medicaments for use in treating various diseases.

BACKGROUND OF THE INVENTION

The natural hormone, 1α,25-dihydroxyvitamin $D_3$ (also referred to as 1α,25-dihydroxycholecalciferol and calcitriol) and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins, and fluorinated analogs. Some of these compounds exhibit an interesting separation of activities in cell differentiation and calcium regulation. This difference in activity is useful in the treatment of a variety of diseases as established in the art, such as renal osteodystrophy, vitamin D-resistant rickets, osteoporosis, psoriasis, and certain malignancies (see for example, Zemplar, Calcipotriol, MC-903, Dovonex, 22-oxa-1a, 25-(OH)$_2$D$_3$). Slatopolsky, E., Finch, J., Ritter, C., Denda, M., Morrissey, J., Brown, A. & DeLuca, H. (1995) Am. J. Kidney Dis. 26, 852-860; Kubodera, N., Sato, K. & Nishii, Y. (1997) in Vitamin D, eds. Feldman, D., Glorieux, F. H. & Pike, J. W. (Academic, New York), Vol. 63, pp. 1071-1086; Calverley, M. J. (1987) Tetrahedron Lett. 43, 4609-4619; Uskokovic, M. R., Studzinski, G. P. & Reddy, S. G. (1997) in Vitamin D, eds. Feldman, D., Glorieux, F. H. & Pike, J. W. (Academic, New York), Vol. 62, pp. 1045-1070; Kensler, T. W., Dolan, P. M., Gange, S. J., Lee, J.-K., Wang, Q. & Posner, G. H. (2000) Carcinogenesis 21, 1341-1345; Binderup, L., Binderup, E. & Godfredsen, W. O. (1997) in Vitamin D, eds. Feldman, D., Glorieux, F. H. & Pike, J. W. (Academic, New York), Vol. 61, pp. 1027-1043; Jones, G. (1997) in Vitamin D, eds. Feldman, D., Glorieux, F. H. & Pike, J. W. (Academic, New York), Vol. 58, pp. 973-994; Brown, A. J. & Slatopolsky, E. (1997) in Vitamin D, eds. Feldman, D., Glorieux, F. H. & Pike, J. W. (Academic, New York), Vol. 59, pp. 995-1009; Shankar, V. N., Propp, A. E., Schroeder, N. S., Surber, B. W., Makin, H. L. J. & Jones, G. (2001) Arch. Biochem. Biophys. 387, 297-306. All these references are incorporated herein by reference for all purposes.

As described above, renal osteodystrophy is a bone disease that occurs when the kidneys fail to maintain the proper levels of calcium and phosphorus in the blood. Renal osteodystrophy is a common problem in people with kidney disease and affects 90 percent of dialysis patients.

Renal osteodystrophy is most serious in children because their bones are still growing. The condition slows bone growth and causes deformities. One such deformity occurs when the legs bend inward toward each other or outward away from each other; this deformity is referred to as "renal rickets." Another important consequence is short stature. Symptoms can be seen in growing children with renal disease even before they start dialysis.

The bone changes from renal osteodystrophy can begin many years before symptoms appear in adults with kidney disease. The symptoms of renal osteodystrophy are not usually seen in adults until they have been on dialysis for several years. Older patients and women who have gone through menopause are at greater risk for this disease because they're already vulnerable to osteoporosis, even without kidney disease. If left untreated, the bones gradually become thin and weak, and a person with renal osteodystrophy begins to experience bone and joint pain and an increased risk of bone fractures.

In healthy adults, bone tissue is continually being remodeled and rebuilt. The kidneys play an important role in maintaining healthy bone mass and structure because it balances calcium and phosphorus levels in the blood. If calcium levels in the blood become too low, the parathyroid glands release parathyroid hormone (PTH). This hormone draws calcium from the bones to raise blood calcium levels. Too much PTH in the blood causes disturbances in calcium and phosphorus homeostasis. This in turn removes too much calcium from the bones; over time, the constant removal of calcium weakens the bones.

Secondary hyperparathyroidism is characterized by an elevation PTH associated with inadequate levels of active vitamin D hormone. Typically, Vitamin D requires two sequential hydroxylations in the liver and the kidney to bind to activate the Vitamin D receptor (VDR). The endogenous VDR activator, calcitriol [1,25(OH)$_2$ D$_3$] is a hormone that binds to VDRs that are present in the parathyroid gland, intestine, kidney, and bone to maintain parathyroid function and calcium and phosphorus homeostasis, and to VDRs found in many other tissues, including prostate, endothelium and immune cells. Phosphorus also helps regulate calcium levels in the bones. Healthy kidneys remove excess phosphorus from the blood. When the kidneys stop working normally, phosphorus levels in the blood can become too high, leading to lower levels of calcium in the blood and resulting in the loss of calcium from the bones.

Healthy kidneys produce calcitriol to help the body absorb dietary calcium into the blood and the bones. If calcitriol levels drop too low, PTH levels increase, and calcium is removed from the bones. Calcitriol and PTH work together to keep calcium balance normal and bones healthy. In a patient with kidney failure, the kidneys stop making calcitriol, dietary calcium is not absorbed and calcium is removed from the bones.

Controlling PTH levels prevents calcium from being withdrawn from the bones. Usually, overactive parathyroid glands are controllable with a change in diet, dialysis treatment, or medication. The drug cinacalcet hydrochloride (Sensipar), approved by the Food and Drug Administration in 2004, lowers PTH levels by binding to the calcium receptor that controls PTH release. If PTH levels cannot be controlled, the parathyroid glands may need to be removed surgically. Other treatments for the condition include taking synthetic calcitriol as a pill or in an injectable form.

Renal osteodystrophy can also be treated with changes in diet. Reducing dietary intake of phosphorus is one of the most important steps in preventing bone disease. Often, medications such as calcium carbonate (Tums), calcium acetate (PhosLo), sevelamer hydrochloride (Renagel), or lanthanum carbonate (Fosrenol) are prescribed with meals and snacks to bind phosphorus in the bowel, which decreases the absorption of phosphorus into the blood.

Other treatment choices for renal osteodystrophy include Paracalcitol, the active ingredient of Zemplar (paracalcitol injection, USP), which is a synthetic, biologically active vitamin D analog of calcitriol with modifications to the side chain and the A (19-nor) ring. Preclinical and in vitro studies have demonstrated that paricalcitol's actions are mediated through binding to the VDR, resulting in the selective activation of Vitamin D response pathways. Calcitriol and paricalcitol have been shown to reduce parathyroid hormone levels by inhibiting PTH synthesis and secretion.

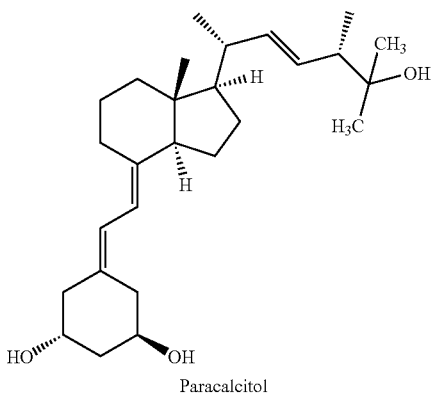 [SMILES: C[C@H](/C=C/[C@H](C)C(C)(C)O)[C@H]1CC[C@H]2/C(=C/C=C3C[C@@H](O)C[C@H](O)C3)CCC[C@]12C]

Paracalcitol

The structure of 1α,25-dihydroxyvitamin $D_3$ and the numbering system used to denote the carbon atoms in this compound are shown below.

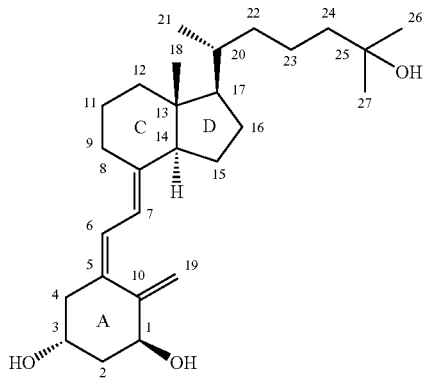

1α,25-Dihydroxyvitamin $D_3$=1α,25-Dihydroxycholecalciferol=Calcitriol

Typically, the class of vitamin D analogs such as 19-nor-vitamin D compounds is characterized by the absence of carbon 19 from the A-ring exocyclic methylene group, typical of the vitamin D system. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. application Ser. Nos. 11/669,029 and 11/669,053 filed on Jan. 30, 2007, (20R,25S)-2-methylene-19,26-dinor-1α,25-dihydroxyvitamin D3 (NEL) and (20S,25S)-2-methylene-19,26-dinor-1α,25-dihydroxyvitamin D3 (RAK) have been described and examined by DeLuca et al. as potential drugs for treatment of renal osteodystrophy. In U.S. Pat. No. 4,666,634, 2β-hydroxy and alkoxy (e.g., ED-71) analogs of 1α,25-dihydroxyvitamin $D_3$ have been described and examined by the Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Various 2-substituted analogs of 1α,25-dihydroxy-19-nor-vitamin $D_3$ have also been synthesized, i.e. compounds substituted at the 2-position with hydroxy or alkoxy groups (DeLuca et al., U.S. Pat. No. 5,536,713), with 2-alkyl groups (DeLuca et al., U.S. Pat. No. 5,945,410), and with 2-alkylidene groups (DeLuca et al., U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs that are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-(20S)-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents. Other 19-nor compounds are disclosed in U.S. patent application Ser. Nos. 10/996,642 and 10/997,698. All these patents and patent applications are incorporated herein by reference for all purposes.

Yet other 19-nor class of pharmacologically important vitamin D analogs that are characterized by the presence of a α-alkyl, α-hydroxyalkyl, β-alkyl or β-hydroxalkyl substituent at carbon 2 (C-2) and a hydroxyl group at carbon 1 (C-1), have been synthesized and tested, as disclosed in U.S. Pat. Nos. 6,846,811, 6,844,457, 6,844,332, 6,844,331, 6,844,330, 6,306,844, 6,277,837, 6,127,559 and 5,945,410. Compounds disclosed in these U.S. Pat. Nos. '811, '457, '332, '331, '330, '844, '837, '559 and '410 are excellent candidates for a variety of pharmaceutical uses as described in these patents. All these patents are incorporated herein by reference for all purposes.

Further certain trinor analogs of Vitamin D have been synthesized and characterized, as described in U.S. Pat. No. 4,970,203, which are excellent candidates for a variety of pharmaceutical uses, as set forth in '203 patents and U.S. Pat. Nos. 6,291,444, 5,880,114 and 4,411,833, which are all incorporated herein for all purposes.

Since the currently available treatments, including compounds and formulations described above have various limitations to a greater or lesser extent, new compounds and pharmaceutical formulations are desirable that continue to decrease the calcemic effect while retaining the ability to suppress PTH.

SUMMARY OF THE INVENTION

The invention generally provides (20R)-2-methylene-19,26,27-trinor-1α,25-dihydroxycalciferol (RA-7), (20R)-2α-methyl-19,26,27-trinor-1α,25-dihydroxycalciferol and (20R)-2β-methyl-19,26,27-trinor-1α,25-dihydroxycalciferol and related compounds, pharmaceutical formulations that include these compounds and the use of these compounds in the preparation of medicaments for use in treating various disease states.

Therefore, in one aspect, the invention provides a compound having the formula I, II or III as shown below:

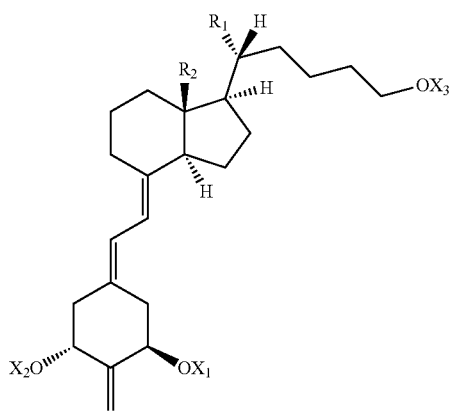

I

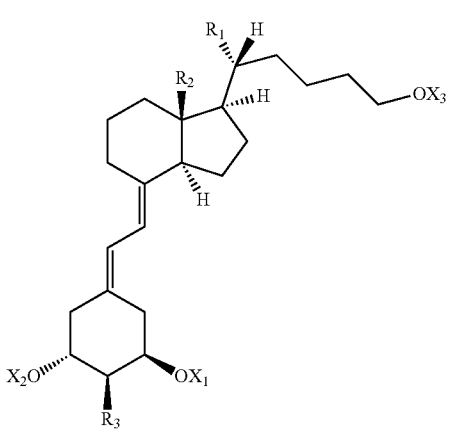

II

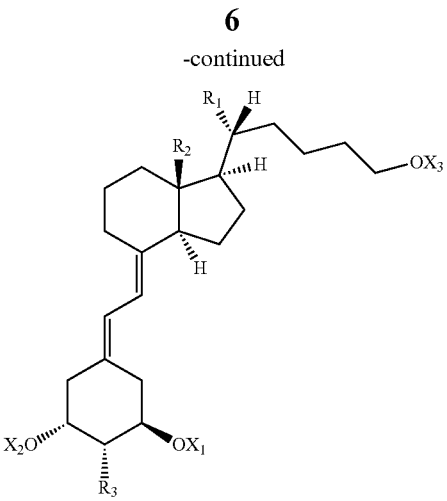

III where $X_1$, $X_2$ and $X_3$ are the same or different groups and are independently selected from H or hydroxy-protecting groups. In some embodiments, $X_1$, $X_2$ and $X_3$ are hydroxy protecting groups such as silyl ether groups, alkyl ether groups, alkoxyalkyl ether group, acetal groups and ester groups. In some such embodiments, $X_1$, $X_2$ and $X_3$ are t-butyldimethylsilyl ether group (TBDMS), trimethylsilyl ether group (TMS), triethylsilyl ether group (TES), Triisopropylsilyl ether group (TIPS), t-butyldiphenylsilyl ether group (TBDPS), tetrahydropyran group (THP), methoxyethoxymethyl group (MEM), methoxymethyl group (MOM), benzyl ether group, t-butyl ether group, N-phthalimido acetal group (Nphth), isopropylidene, trimethoxy butane, 2,4-dimethyl-pentan-3-yloxycarbonyl group (Doc). Various other hydroxy protecting groups are known to one of ordinary skill in the art, for example see Jarowicki et al, J. Chem. Soc., Perkin Trans. 1, 1998, 4005-4037, which is incorporated herein by reference for all purposes.

In this aspect of the invention, $R_1$, $R_2$ and $R_3$ are the same or different groups and are independently selected from straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms. In some such embodiments, $R_1$, $R_2$ and $R_3$ are selected from straight or branched chain alkyl groups having from 2 to 7 carbon atoms, straight or branched chain alkenyl groups having from 2 to 7 carbon atoms, straight or branched chain hydroxy-substituted alkyl groups having from 2 to 6 carbon atoms, or straight or branched chain hydroxy-substituted alkenyl groups having from 2 to 6 carbon atoms. In other such embodiments, $R_1$, $R_2$ and $R_3$ are selected from straight or branched chain alkyl groups having from 2 to 7 carbon atoms, straight or branched chain alkenyl groups having from 2 to 7 carbon atoms, or straight or branched chain hydroxy-substituted alkenyl groups having from 2 to 6 carbon atoms. In certain embodiments, $R_1$ or $R_2$ or both $R_1$ and $R_2$ may be H independent of each other.

As used herein, the phrase "straight and branched chain alkyl groups" refers to groups that include carbon and hydrogen atoms that only include carbon-carbon single bonds and carbon-hydrogen single bonds. These groups do not include any heteroatoms (atoms other than H or C). Thus, the phrase "straight and branched chain alkyl groups" includes straight chain alkyl groups such as methyl, ethyl, propyl, butyl, pentyl, hexyl, heptyl, and octyl groups and branched chain isomers of straight chain alkyl groups, including but not limited to, the following which are provided by way of example only: —CH(CH₃)₂, —CH(CH₃)(CH₂CH₃), —CH(CH₂CH₃)₂, —C(CH₃)₃, —C(CH₂CH₃)₃, —CH₂CH(CH₃)₂, —CH₂CH (CH₃)(CH₂CH₃), —CH₂CH(CH₂CH₃)₂, —CH₂C(CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH (CH₃)CH₂CH(CH₃)₂, —CH(CH₃)CH₂CH(CH₃)₂, —CH₂CH₂CH₂C(CH₃)₃, —CH₂CH₂CH₂CH(CH₃)₂, —CH₂CH₂CH(CH₃)C(CH₃)₃, —CH₂CH₂CH(CH₃)CH (CH₃)₂, and the like.

As used herein, the phrase "hydroxy-substituted alkyl groups" refers to "straight and branched chain alkyl groups" as defined above in which a bond to a carbon or a hydrogen atom is replaced by a bond to a hydroxyl (—OH) group.

As used herein, the phrase "straight and branched chain alkenyl groups" refers to "straight and branched chain alkyl groups" as defined above, except that at least one double bond exists between two of the carbon atoms. Examples include, but are not limited to the cis and trans (Z and E) isomers of —CH=CH₂, —CH=C(H)(CH₃), —CH=C(CH₃)₂, —C(CH₃)=C(H)₂, —C(CH₃)=C(H)(CH₃), —C(CH₂CH₃)=CH₂, —C(H)=C(H)CH₂CH(CH₃)₂, —C(H)=C(H)CH (CH₃)CH(CH₃)₂, —C(H)=C(H)CH₂C(CH₃)₃, —C(H)=C (H)CH(CH₃)C(CH₃)₃, and the like.

As used herein, the phrase "hydroxy-substituted alkenyl groups" has the same meaning with respect to "straight and branched chain alkenyl groups" that "hydroxy-substituted alkyl groups" had with respect to "straight and branched chain alkyl groups". Therefore, "hydroxy-substituted alkenyl groups" are "straight and branched chain alkenyl groups" in which a bond to a hydrogen atom or carbon atom that is not double-bonded to another carbon atom is replaced by a bond to a hydroxyl (—OH) group.

Generally, as used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality is found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

In other embodiments, $X_1$, $X_2$ and $X_3$ are H and $R_1$, $R_2$ and $R_3$ are CH₃ such that the compounds are (20R)-2-methylene-19,26,27-trinor-1α,25-dihydroxycalciferol (RA-7), (20R)-2α-methyl-19,26,27-trinor-1α,25-dihydroxycalciferol and (20R)-2β-methyl-19,26,27-trinor-1α,25-dihydroxycalciferol having the formula IA, IIA and IIIA as shown below:

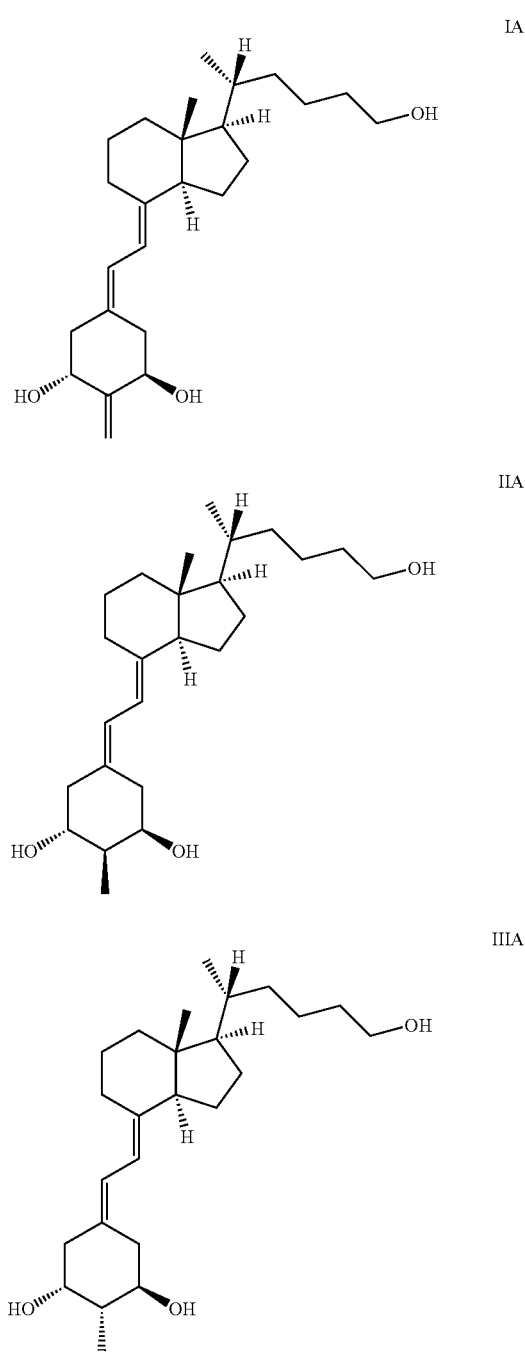

Another embodiment of the present invention provides a pharmaceutical composition, comprising an effective amount of the compound of formula IA, IIA, or IIIA and a pharmaceutically acceptable carrier. In this pharmaceutical composition the effective amount comprises from about 0.01 μg to about 1 mg of the compound per gram of the composition. More preferably, the effective amount comprises from about 0.1 μg to about 500 μg of the compound per gram of the composition.

In certain embodiments, the present invention provides a method of treating a subject suffering from a biological condition, comprising administering an effective amount of the compound of formula I, II, III, or more preferably the compound of formula IA, IIA, or IIIA to the subject, wherein the biological condition is selected from psoriasis; leukemia; colon cancer; breast cancer; skin cancer, lung cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases selected from celiac disease, ulcerative colitis and Crohn's disease; a skin condition selected from wrinkles, lack of adequate skin firmness, lack of adequate dermal hydration, or insufficient sebum secretion; renal osteodystrophy; or osteoporosis. In a preferred embodiment, the biological condition is renal osteodystrophy, vitamin D-resistant rickets, osteoporosis or psoriatic arthritis. In another preferred embodiment, the biological condition is selected from leukemia, colon cancer, breast cancer, skin cancer, lung cancer or prostate cancer. In yet another preferred embodiment, the biological condition is selected from multiple sclerosis, lupus, diabetes mellitus, host versus graft reaction, or rejection of organ transplants. In still other preferred embodiment, the biological condition is selected from rheumatoid arthritis, asthma, or inflammatory bowel diseases selected from celiac disease, ulcerative colitis and Crohn's disease. In yet other preferred embodiment, the biological condition is selected from wrinkles, lack of adequate skin firmness, lack of adequate dermal hydration, or insufficient sebum secretion.

Also preferably, in this embodiment, the effective amount of the compound is administered orally, parenterally, transdermally, nasally, rectally, sublingually or topically to the subject. Yet more preferably, the effective amount of the compound is administered intraperitoneally. In this embodiment, the compound is administered in a dosage of from 0.01 μg per day to 1 mg per day.

Another aspect of the invention provides the use of the compound of formula I, II, III, IA, IIA, or IIIA in the preparation of a medicament for the treatment of a biological condition selected from psoriasis; leukemia; colon cancer; breast cancer; prostate cancer; skin cancer; lung cancer; multiple sclerosis; lupus; diabetes mellitus; host versus graft reaction; rejection of organ transplants; an inflammatory disease selected from rheumatoid arthritis, asthma, or inflammatory bowel diseases selected from celiac disease, ulcerative colitis and Crohn's disease; a skin condition selected from wrinkles, lack of adequate skin firmness, lack of adequate dermal hydration, or insufficient sebum secretion; renal osteodystrophy; osteopenia; or osteoporosis.

Yet another preferred embodiment of the present invention provides the compound having the formula IA

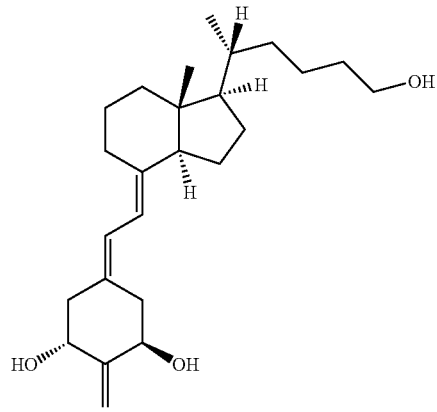

The invention also teaches a pharmaceutical composition having an effective amount of the compound of formula IA and a pharmaceutically acceptable carrier.

Another aspect of the invention provides the use of the compound of formula IA in the preparation of a medicament for the treatment of a biological condition selected from psoriasis; leukemia; colon cancer; breast cancer; prostate cancer; skin cancer; lung cancer; multiple sclerosis; lupus; diabetes mellitus; host versus graft reaction; rejection of organ transplants; an inflammatory disease selected from rheumatoid arthritis, asthma, or inflammatory bowel diseases selected from celiac disease, ulcerative colitis and Crohn's disease; a skin condition selected from wrinkles, lack of adequate skin firmness, lack of adequate dermal hydration, or insufficient sebum secretion; renal osteodystrophy; osteopenia; or osteoporosis.

Further objects, features and advantages of the invention will be apparent from the following detailed description, drawings and appended claims.

BRIEF DESCRIPTION OF THE DRAWINGS

FIG. 1 is a graph comparing the relative activity of RA-7 and 1,25(OH)$_2$D$_3$ to compete for binding with [$^3$H]-1,25-(OH)-2-D$_3$ to the full-length recombinant rat vitamin D receptor.

FIG. 2 is a bar graph comparing the bone calcium mobilization activity of RA-7 with that of 1,25(OH)$_2$D$_3$.

FIG. 3 is a bar graph comparing the intestinal calcium transport activity of RA-7 with that of 1,25(OH)$_2$D$_3$.

FIG. 4 is a graph comparing the percent HL-60 cell differentiation as a function of the concentration of RA-7 with that of 1,25(OH)$_2$D$_3$.

FIG. 5 is a graph comparing the in vitro transcription activity of RA-7 with that of 1,25(OH)$_2$D$_3$.

DETAILED DESCRIPTION OF THE INVENTION

Figure 1:
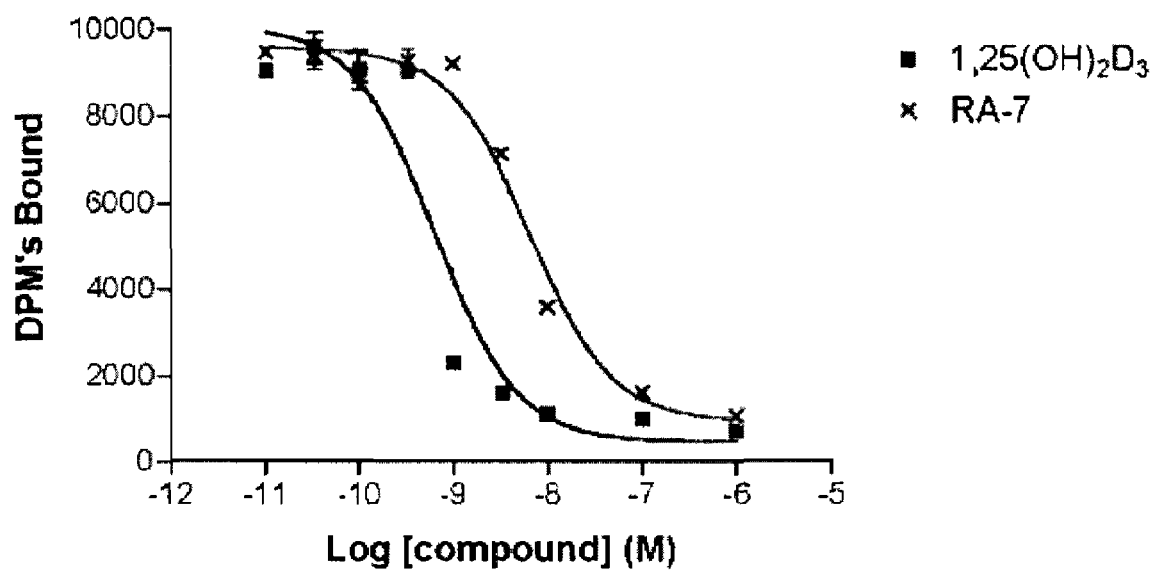
FIGS. 1-5 illustrate various biological activities of (20R)-2-methylene-19,26,27-trinor-1α,25-dihydroxycalciferol (referred to as "RA-7" in the Figures) compared with those of the native hormone 1α,25-dihydroxyvitamin $D_3$ (referred to as "1,25(OH)$_2$D$_3$" in the Figures).

Generally, the invention provides a compound having the formula I, II or III as shown below:

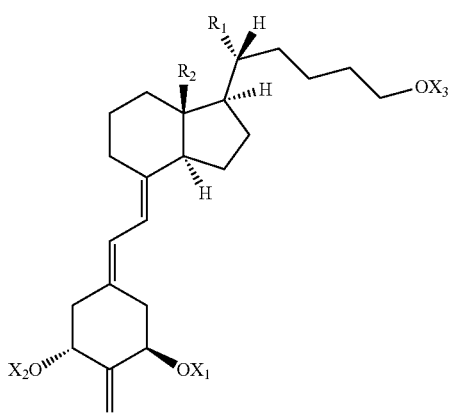

where $X_1$, $X_2$ and $X_3$ are the same or different groups and are independently selected from H or hydroxy-protecting groups. In some embodiments, $X_1$, $X_2$ and $X_3$ are hydroxy protecting groups such as silyl ether groups, alkyl ether groups, alkoxyalkyl ether group, acetal groups and ester groups. In some such embodiments, $X_1$, $X_2$ and $X_3$ are t-butyldimethylsilyl ether group (TBDMS), trimethylsilyl ether group (TMS), triethylsilyl ether group (TES), Triisopropylsilyl ether group (TIPS), t-butyldiphenylsilyl ether group (TBDPS), tetrahydropyran group (THP), methoxyethoxymethyl group (MEM), methoxymethyl group (MOM), benzyl ether group, t-butyl ether group, N-phthalimido acetal group (Nphth), isopropylidene, trimethoxy butane, 2,4-dimethylpentan-3-yloxycarbonyl group (Doc). As discussed above, various other hydroxy protecting groups are known to one of ordinary skill in the art, for example see Jarowicki et al, J. Chem. Soc., Perkin Trans. 1, 1998, 4005-4037, which is incorporated herein by reference for all purposes.

In this aspect of the invention, $R_1$, $R_2$ and $R_3$ are the same or different groups and are independently selected from straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms. In some such embodiments, $R_1$, $R_2$ and $R_3$ are selected from straight or branched chain alkyl groups having from 2 to 7 carbon atoms, straight or branched chain alkenyl groups having from 2 to 7 carbon atoms, straight or branched chain hydroxy-substituted alkyl groups having from 2 to 6 carbon atoms, or straight or branched chain hydroxy-substituted alkenyl groups having from 2 to 6 carbon atoms. In other such embodiments, $R_1$, $R_2$ and $R_3$ are selected from straight or branched chain alkyl groups having from 2 to 7 carbon atoms, straight or branched chain alkenyl groups having from 2 to 7 carbon atoms, or straight or branched chain hydroxy-substituted alkenyl groups having from 2 to 6 carbon atoms. In certain embodiments, $R_1$ or $R_2$ or both $R_1$ and $R_2$ may be H independent of each other.

As used herein, the phrase "straight and branched chain alkyl groups" refers to groups that include carbon and hydrogen atoms that only include carbon-carbon single bonds and carbon-hydrogen single bonds. These groups do not include any heteroatoms (atoms other than H or C). Thus, the phrase "straight and branched chain alkyl groups" includes straight chain alkyl groups such as methyl, ethyl, propyl, butyl, pentyl, hexyl, heptyl, and octyl groups and branched chain isomers of straight chain alkyl groups, including but not limited to, the following which are provided by way of example only: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH(CH$_3$)CH$_2$CH(CH$_3$)$_2$, —CH(CH$_3$)CH(CH$_3$)CH(CH$_3$)$_2$, —CH$_2$CH$_2$CH$_2$C(CH$_3$)$_3$, —CH$_2$CH$_2$CH$_2$CH(CH$_3$)$_2$, —CH$_2$CH$_2$CH(CH$_3$)C(CH$_3$)$_3$, —CH$_2$CH$_2$CH(CH$_3$)CH(CH$_3$)$_2$, and the like.

As used herein, the phrase "hydroxy-substituted alkyl groups" refers to "straight and branched chain alkyl groups" as defined above in which a bond to a carbon or a hydrogen atom is replaced by a bond to a hydroxyl (—OH) group.

As used herein, the phrase "straight and branched chain alkenyl groups" refers to "straight and branched chain alkyl groups" as defined above, except that at least one double bond exists between two of the carbon atoms. Examples include, but are not limited to the cis and trans (Z and E) isomers of —CH═CH$_2$, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, —C(H)═C(H)CH$_2$CH(CH$_3$)$_2$, —C(H)═C(H)CH(CH$_3$)CH(CH$_3$)$_2$, —C(H)═C(H)CH$_2$C(CH$_3$)$_3$, —C(H)═C(H)CH(CH$_3$)C(CH$_3$)$_3$, and the like.

As used herein, the phrase "hydroxy-substituted alkenyl groups" has the same meaning with respect to "straight and branched chain alkenyl groups" that "hydroxy-substituted alkyl groups" had with respect to "straight and branched chain alkyl groups". Therefore, "hydroxy-substituted alkenyl groups" are "straight and branched chain alkenyl groups" in which a bond to a hydrogen atom or carbon atom that is not double-bonded to another carbon atom is replaced by a bond to a hydroxyl (—OH) group.

Generally, as used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality is found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

In other embodiments, $X_1$, $X_2$ and $X_3$ are H and $R_1$, $R_2$ and $R_3$ are $CH_3$ such that the compounds are (20R)-2-methylene-19,26,27-trinor-1α,25-dihydroxycalciferol (RA-7), (20R)-2α-methyl-19,26,27-trinor-1α,25-dihydroxycalciferol and (20R)-2β-methyl-19,26,27-trinor-1α,25-dihydroxycalciferol having the formula IA, IIA and IIIA as shown below:

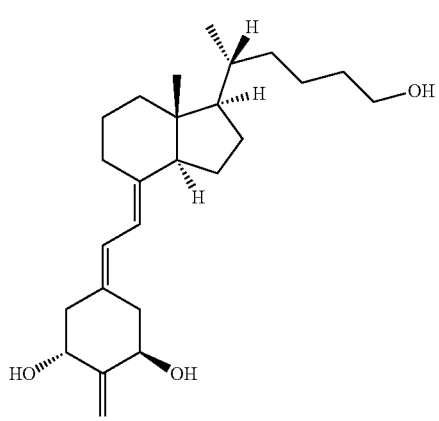

IA

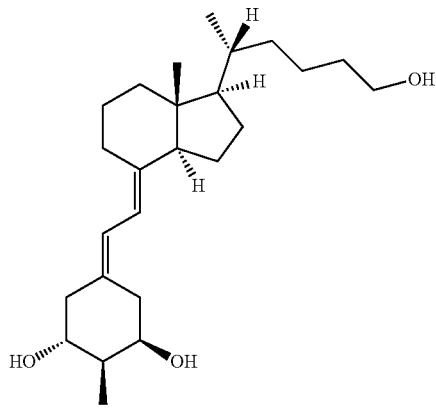

IIA

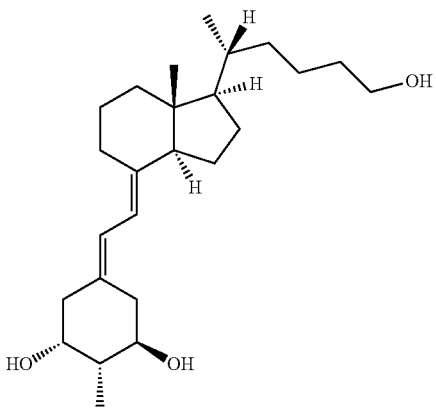

IIIA

The compound of formula IA (RA-7) exhibits a desired, and highly advantageous, pattern of biological activity. This compound is characterized by high binding to vitamin D receptors, as well as good activity in inhibiting the proliferation and causing the differentiation of the cancerous HL-60 cell. Further this compound is characterized by very low intestinal calcium transport activity, as compared to that of 1α,25-dihydroxyvitamin $D_3$, and has very low ability to mobilize calcium from bone, as compared to 1,25-dihydroxyvitamin $D_3$. Hence, this compound can be characterized as having little, if any, calcemic activity. Thus, it is useful as a therapy for suppression of secondary hyperparathyroidism or renal osteodystrophy.

Compounds IIA and IIIA are also expected to have highly advantageous pattern of biological activity based on the 2α-alkyl and 2β-alkyl substituents, comparable to other Vitamin D analogs having α-alkyl, α-hydroxyalkyl, β-alkyl or β-hydroxyalkyl substituent at carbon 2 (C-2) and a hydroxyl group at carbon 1 (C-1), which have been synthesized and tested, and are disclosed in U.S. Pat. Nos. 6,846,811, 6,844,457, 6,844,332, 6,844,331, 6,844,330, 6,306,844, 6,277,837, 6,127,559 and 5,945,410. Compounds disclosed in these U.S. Pat. Nos. '811, '457, '332, '331, '330, '844, '837, '559 and '410 are excellent candidates for a variety of pharmaceutical uses as described in these patents.

In an exemplary embodiment, compound RA-7 of the invention is also especially suited for treatment and prophylaxis of human disorders which are characterized by an imbalance in the immune system, e.g. in autoimmune diseases, including multiple sclerosis, lupus, diabetes mellitus, host versus graft reaction, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which are treated with the compound of the invention.

The above compound RA-7 is also characterized by relatively high cell differentiation activity. Thus, this compound also provides a therapeutic agent for the treatment of psoriasis, or as an anti-cancer agent, especially against leukemia, colon cancer, breast cancer, skin cancer, lung cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

The compounds of the invention are used to prepare pharmaceutical formulations or medicaments that include a compound of the invention in combination with a pharmaceutically acceptable carrier. Such pharmaceutical formulations and medicaments are used to treat various biological disorders such as those described herein. Methods for treating such disorders typically include administering an effective amount of the compound or an appropriate amount of a pharmaceutical formulation or a medicament that includes the compound to a subject suffering from the biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

The compounds present in a composition to treat the above-noted diseases and disorders are in an amount from about 0.01 μg/gm to about 1 mg/gm of the composition, preferably from about 0.1 μg/gm to about 500 μg/gm of the composition, and is administered topically, transdermally, orally, or parenterally in dosages of from about 0.01 μg/day to about 1 mg/day, preferably from about 0.1 μg/day to about 500 μg/day.

One preferred embodiment of the present invention provides the compound having the formula IA

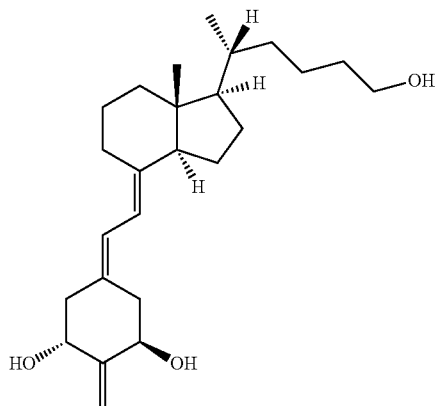

IA

In a preferred embodiment, (20R)-2-methylene-19,26,27-trinor-1α,25-dihydroxycalciferol (13) (RA-7) was synthesized, and tested, and is useful in treating a variety of biological conditions as described herein.

Generally, preparation of (20R)-2-methylene-19,26,27-trinor-1α,25-dihydroxycalciferol (13) (RA-7), (20R)-2α-methyl-19,26,27-trinor-1α,25-dihydroxycalciferol and (20R)-2β-methyl-19,26,27-trinor-1α,25-dihydroxycalciferol can be accomplished by condensing an appropriate bicyclic Windaus-Grundmann type ketone (III) with the allylic phosphine oxide IV followed by deprotection (removal of the $Y_1$ and $Y_2$ groups). Other compounds of the present invention are similarly synthesized.

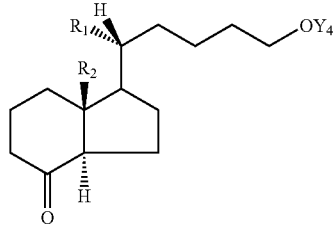

III

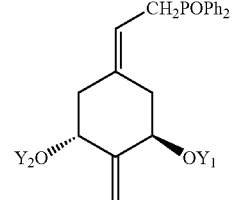

IV

In the ketone III and the phosphine oxide IV, $Y_1$, $Y_2$, $Y_4$ are preferably hydroxy-protecting groups where $X_1$, $X_2$ and $X_3$ are the same or different groups and are independently selected from H or hydroxy-protecting groups. In some embodiments, $X_1$, $X_2$ and $X_3$ are hydroxy protecting groups such as silyl ether groups, alkyl ether groups, alkoxyalkyl ether group, acetal groups and ester groups. In some such embodiments, $X_1$, $X_2$ and $X_3$ are t-butyldimethylsilyl ether group (TBDMS), trimethylsilyl ether group (TMS), triethylsilyl ether group (TES), Triisopropylsilyl ether group (TIPS), t-butyldiphenylsilyl ether group (TBDPS), tetrahydropyran group (THP), methoxyethoxymethyl group (MEM), methoxymethyl group (MOM), benzyl ether group, t-butyl ether group, N-phthalimido acetal group (Nphth), isopropylidene, trimethoxy butane, 2,4-dimethylpentan-3-yloxycarbonyl group (Doc). Various other hydroxy protecting groups are known to one of ordinary skill in the art, for example see Jarowicki et al, J. Chem. Soc., Perkin Trans. 1, 1998, 4005-4037, which is incorporated herein by reference for all purposes.

In a preferred embodiment, the triethylsilyl group (TES) and t-butyldimethylsilyl (TBDMS) group are examples of a particularly useful hydroxy-protecting groups. The process described above represents an application of the convergent synthesis concept, which has been applied effectively to the preparation of numerous vitamin D compounds (see Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

Further, in ketone III, $R_1$ and $R_2$ groups are same or different, and are independently selected from H or straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms. In some such embodiments, $R_1$ and $R_2$ are selected from H or straight or branched chain alkyl groups having from 2 to 7 carbon atoms, straight or branched chain alkenyl groups having from 2 to 7 carbon atoms, straight or branched chain hydroxy-substituted alkyl groups having from 2 to 6 carbon atoms, or straight or branched chain hydroxy-substituted alkenyl groups having from 2 to 6 carbon atoms. In other such embodiments, $R_1$ and $R_2$ are selected from H or straight or branched chain alkyl groups having from 2 to 7 carbon atoms, straight or branched chain alkenyl groups having from 2 to 7 carbon atoms, or straight or branched chain hydroxy-substituted alkenyl groups having from 2 to 6 carbon atoms.

As used herein, the phrase "straight and branched chain alkyl groups" refers to groups that include carbon and hydrogen atoms that only include carbon-carbon single bonds and carbon-hydrogen single bonds. These groups do not include any heteroatoms (atoms other than H or C). Thus, the phrase "straight and branched chain alkyl groups" includes straight chain alkyl groups such as methyl, ethyl, propyl, butyl, pentyl, hexyl, heptyl, and octyl groups and branched chain isomers of straight chain alkyl groups, including but not limited to, the following which are provided by way of example only: —$CH(CH_3)_2$, —$CH(CH_3)(CH_2CH_3)$, —$CH(CH_2CH_3)_2$, —$C(CH_3)_3$, —$C(CH_2CH_3)_3$, —$CH_2CH(CH_3)_2$, —$CH_2CH(CH_3)(CH_2CH_3)$, —$CH_2CH(CH_2CH_3)_2$, —$CH_2C(CH_3)_3$, —$CH_2C(CH_2CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, —$CH(CH_3)CH_2CH(CH_3)_2$, —$CH(CH_3)CH(CH_3)CH(CH_3)_2$, —$CH_2CH_2CH_2C(CH_3)_3$, —$CH_2CH_2CH_2CH(CH_3)_2$, —$CH_2CH_2CH(CH_3)C(CH_3)_3$, —$CH_2CH_2CH(CH_3)CH(CH_3)_2$, and the like.

As used herein, the phrase "hydroxy-substituted alkyl groups" refers to "straight and branched chain alkyl groups" as defined above in which a bond to a carbon or a hydrogen atom is replaced by a bond to a hydroxyl (—OH) group.

As used herein, the phrase "straight and branched chain alkenyl groups" refers to "straight and branched chain alkyl groups" as defined above, except that at least one double bond exists between two of the carbon atoms. Examples include, but are not limited to the cis and trans (Z and E) isomers of —$CH=CH_2$, —$CH=C(H)(CH_3)$, —$CH=C(CH_3)_2$, —$C(CH_3)=C(H)_2$, —$C(CH_3)=C(H)(CH_3)$, —$C(CH_2CH_3)=CH_2$, —$C(H)=C(H)CH_2CH(CH_3)_2$, —$C(H)=C(H)CH(CH_3)CH(CH_3)_2$, —$C(H)=C(H)CH_2C(CH_3)_3$, —$C(H)=C(H)CH(CH_3)C(CH_3)_3$, and the like.

As used herein, the phrase "hydroxy-substituted alkenyl groups" has the same meaning with respect to "straight and branched chain alkenyl groups" that "hydroxy-substituted alkyl groups" had with respect to "straight and branched chain alkyl groups". Therefore, "hydroxy-substituted alkenyl groups" are "straight and branched chain alkenyl groups" in which a bond to a hydrogen atom or carbon atom that is not double-bonded to another carbon atom is replaced by a bond to a hydroxyl (—OH) group.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality is found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

Phosphine oxide IV is a convenient reagent that can be used to prepare a large number of 19-nor vitamin D compounds and is prepared according to the procedures described by Sicinski et al., J. Med. Chem., 41, 4662 (1998), DeLuca et al., U.S. Pat. No. 5,843,928; Perlman et al., Tetrahedron Lett. 32, 7663 (1991); and DeLuca et al., U.S. Pat. No. 5,086,191. Scheme I shows the general procedure for synthesizing phosphine oxide IV as outlined in U.S. Pat. No. 5,843,928 which is hereby incorporated by reference in its entirety as if fully set forth herein. Modification of the method shown in Scheme I is used to produce a large number of vitamin D analogs as will be apparent to those skilled in the art. For example, a wide variety of phosphonium compounds is used in place of the MePh$_3$P$^+$Br$^-$ used to convert ketone B to alkene C. Examples of such compounds include EtPh$_3$P$^+$Br$^-$, PrPh$_3$P$^+$Br$^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in an analogous manner to that used to prepare phosphine oxide H in Scheme I. Alternatively, an alkene analogous to compound C of Scheme I is reduced with (Ph$_3$P)$_3$RhCl and H$_2$ to provide other vitamin D analogs. See U.S. Pat. No. 5,945,410 and Sicinski, R. R. et al., J. Med. Chem., 41, 4662-4674 (1998) both of which are hereby incorporated by reference in their entireties and for all purposes. Therefore, the procedure for forming the phosphine oxide shown in Scheme I is used to prepare a wide variety of vitamin D analogs in addition to the compound of the present invention.

Scheme I

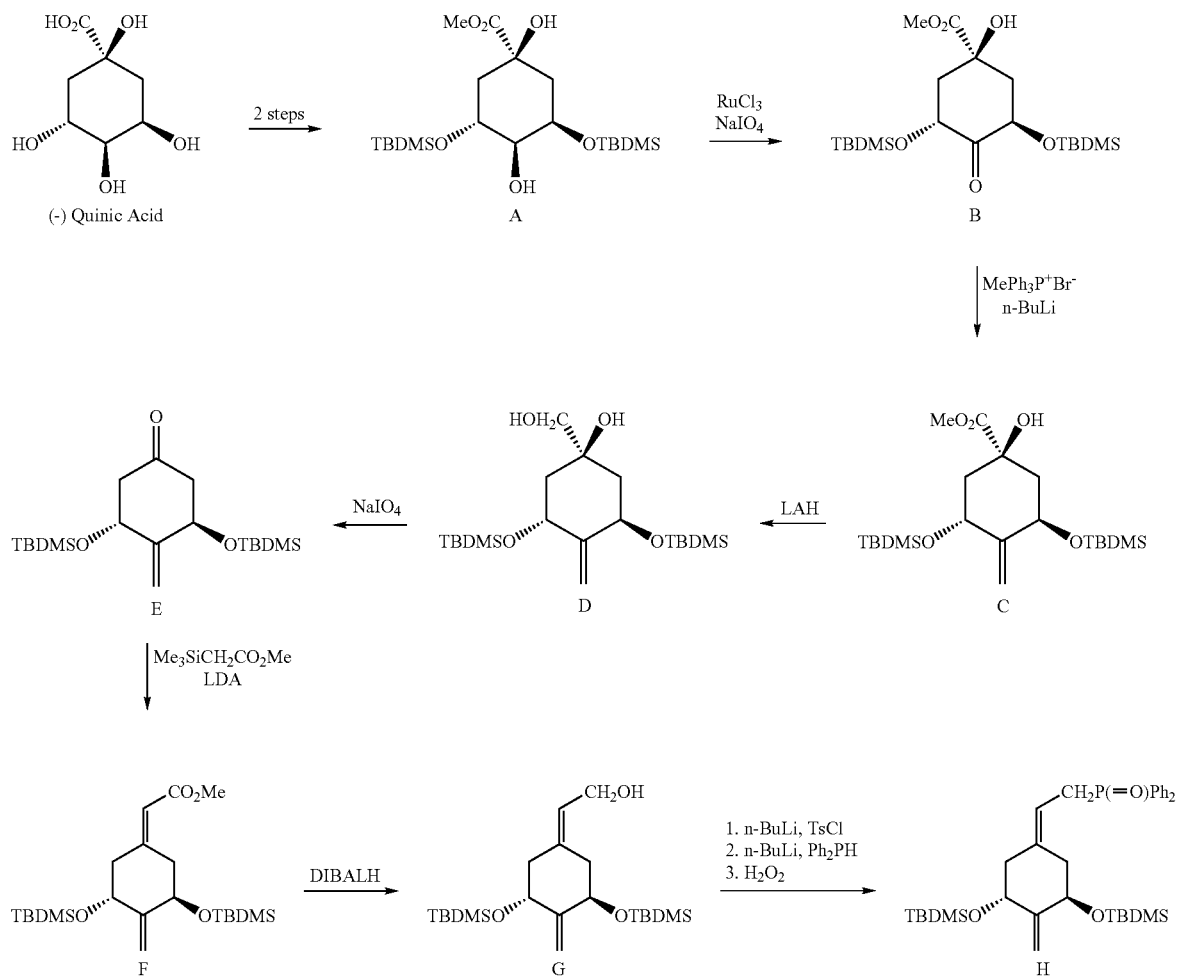

Hydraindanones of structure III can prepared by known methods or adapted methods as will be readily apparent to one of skill in the art and described herein. Specific examples of some important bicyclic ketones used to synthesize vitamin D analogs are those described in Mincione et al., Synth. Commun 19, 723, (1989); and Peterson et al., J. Org. Chem. 51, 1948, (1986).

In one preferred embodiment, ketone III having $Y_4$=TBSO (10) group is synthesized by the Schemes II and III, as shown below:

Scheme II

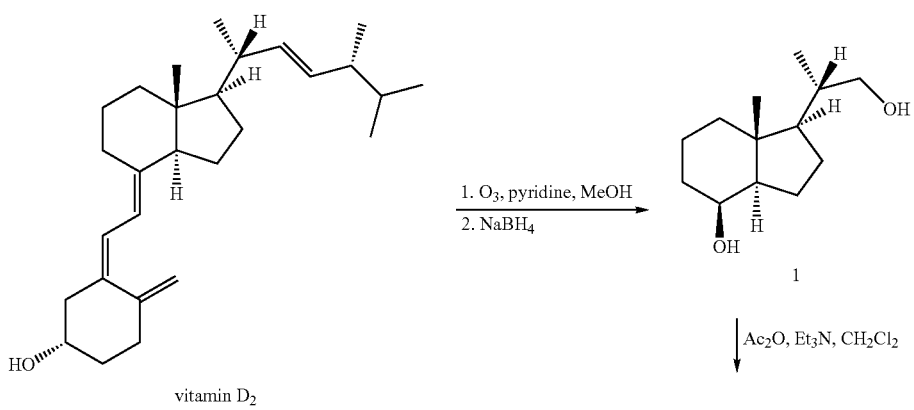

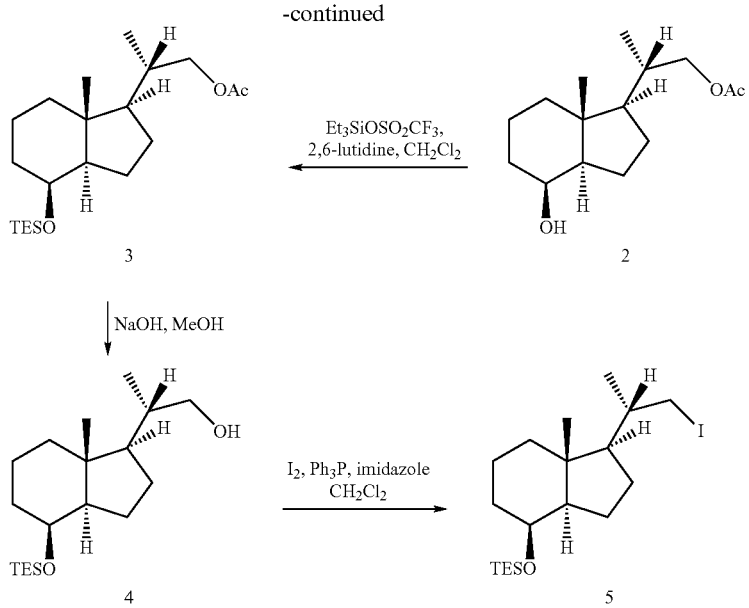
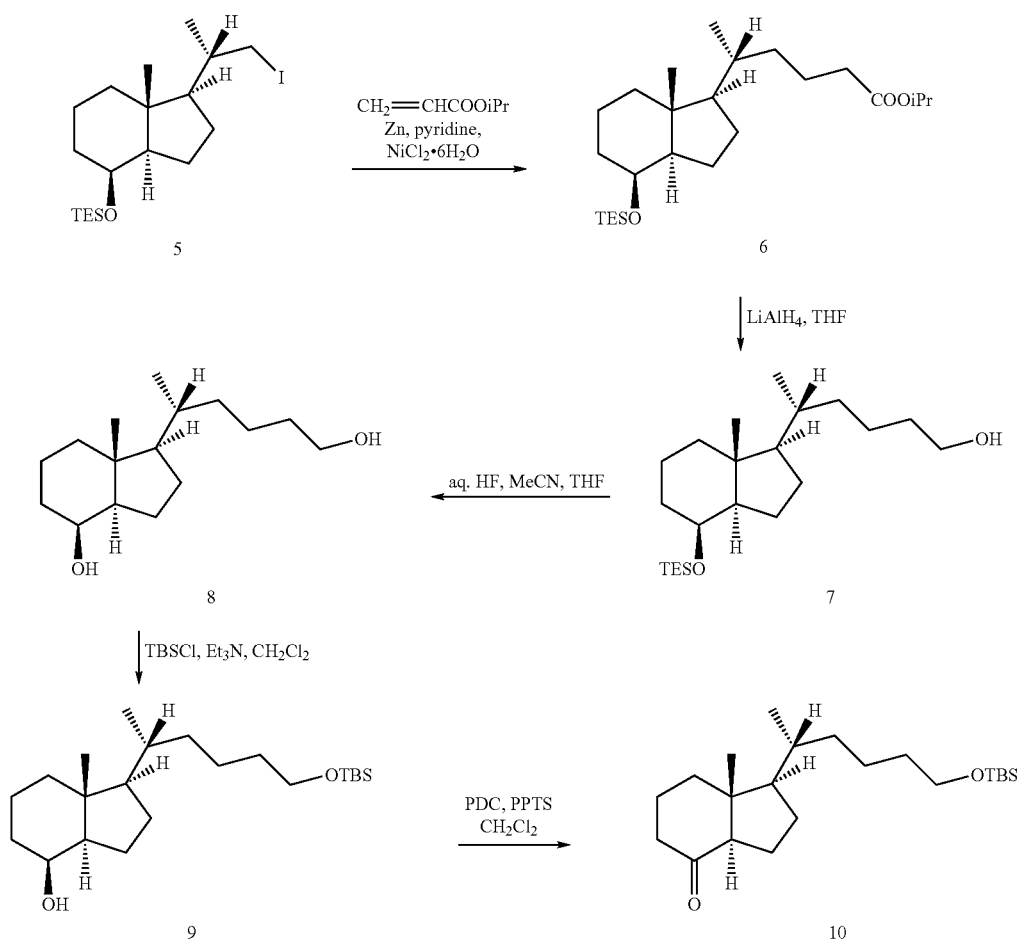

Further, compounds (20R)-2-methylene-19,26,27-trinor-1α,25-dihydroxycalciferol (13) (RA-7), (20R)-2α-methyl-19,26,27-trinor-1α,25-dihydroxycalciferol (14) and (20R)-2β-methyl-19,26,27-trinor-1α,25-dihydroxycalciferol (15) are synthesized as shown below in Scheme IV An overall process for synthesizing various 2-alkylidene-19-nor-vitamin D compounds is illustrated and described in U.S. Pat. No. 5,843,928, U.S. Pat. No. 6,627,622, U.S. Pat. No. 6,579,861, U.S. Pat. No. 5,086,191, U.S. Pat. No. 5,585,369, and U.S. Pat. No. 6,537,981 and Andrzej R. Daniewski

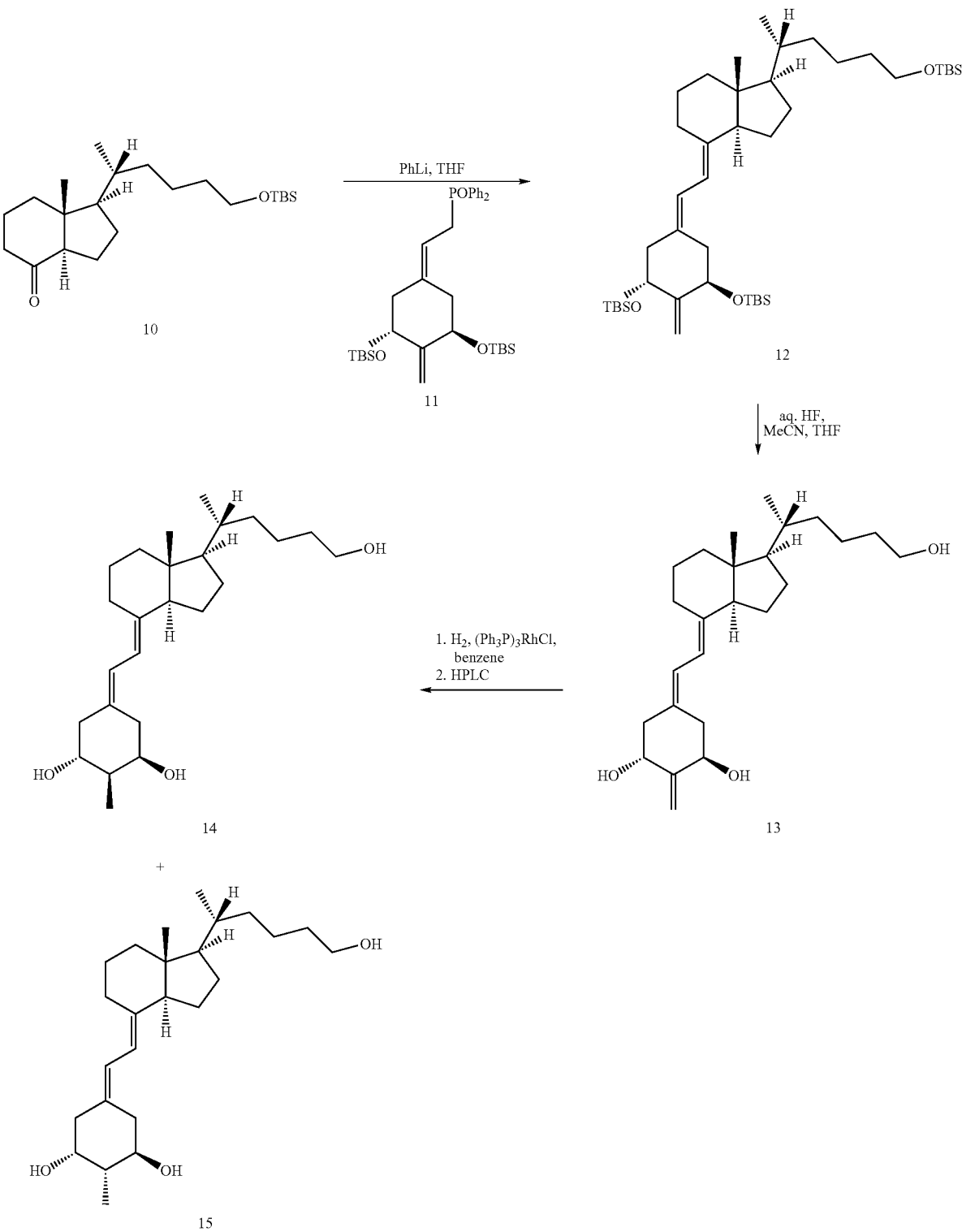

and Wen Liu, J. Org. Chem. 66, 626-628 (2001), which are hereby incorporated by reference in its entirety and for all purposes as if fully set forth herein.

Compounds of formula I, II, III, IA, IIA and IIIA can be prepared using the methods shown in Schemes I, II, III and IV.

Following examples illustrate synthesis and biological activity of the selected compounds provided in the present invention. These Examples are for illustration purposes only and should not be deemed to limit the scope of the invention.

Example I

RA-7 Synthesis

Preparation of (8S,20S)-de-A,B-20-(hydroxymethyl)-pregnan-8-ol (1)

Ozone was passed through a solution of vitamin $D_2$ (3 g, 7.6 mmol) in methanol (250 mL) and pyridine (2.44 g, 2.5 mL, 31 mmol) for 50 min at −78 °C. The reaction mixture was then flushed with an oxygen for 15 min to remove the residual ozone and the solution was treated with $NaBH_4$ (0.75 g, 20 mmol). After 20 min the second portion of $NaBH_4$ (0.75 g, 20 mmol) was added and the mixture was allowed to warm to room temperature. The third portion of $NaBH_4$ (0.75 g, 20 mmol) was then added and the reaction mixture was stirred for 18 h. The reaction was quenched with water (40 mL) and the solution was concentrated under reduced pressure. The residue was extracted with ethyl acetate (3×80 mL) and the combined organic phase washed with 1M aq. HCl, saturated aq. $NaHCO_3$, dried ($Na_2SO_4$) and concentrated under reduced pressure. The residue was chromatographed on silica gel with hexane/ethyl acetate (75:25) to give the diol 1 (1.21 g, 75% yield) as white crystals:

m.p. 106-108° C.; $[\alpha]_D$+30.2° (c 1.46, $CHCl_3$); $^1H$ NMR (400 MHz, $CDCl_3$) δ 4.08 (1H, d, J=2.0 Hz, 8α-H), 3.63 (1H, dd, J=10.5, 3.1 Hz, 22-H), 3.38 (1H, dd, J=10.5, 6.8 Hz, 22-H), 1.99 (1H, br.d, J=13.2 Hz), 1.03 (3H, d, J=6.6 Hz, 21-$H_3$), 0.956 (3H, s, 18-$H_3$); $^{13}C$ NMR (100 MHz) δ 69.16 (d, C-8), 67.74 (t, C-22), 52.90 (d), 52.33 (d), 41.83 (s, C-13), 40.19 (t), 38.20 (d), 33.53 (t), 26.62 (t), 22.54 (t), 17.36 (t), 16.59 (q, C-21), 13.54 (q, C-18); MS (EI) m/z 212 (2, M$^+$), 194 (34, M$^+$-$H_2O$), 179 (33, M$^+$-$H_2O$—$CH_3$), 163 (18, M$^+$-$CH_2OH$—$H_2O$), 135 (36), 125 (54), 111 (100), 95 (63), 81 (67); exact mass calculated for $C_{13}H_{22}O$ (M$^+$-$H_2O$) 194.1671. found 194.1665.

Preparation of (8S,20S)-de-A, -20-(acetyloxymethyl)-pregnan-8-ol (2)

Acetic anhydride (1.05 mL, 1.13 g, 11.1 mmol) was added to a solution of the diol 1 (1.8 g, 8.5 mmol) and triethylamine (4.2 mL, 3.03 g, 30 mmol) in anhydrous dichloromethane (10 mL) at 0° C. The mixture was stirred under argon at room temperature for 18 h. The reaction was quenched with water (10 mL) and extracted with dichloromethane. The combined organic phase washed with brine, dried ($Na_2SO_4$) and concentrated under reduced pressure. The pure alcohol 2 (2.09 g, 97% yield) was isolated by a chromatography on silica gel with hexane/ethyl acetate (95:5, then 9:1), as a colorless oil:

$[\alpha]_D$+34.4° (c 1.63, $CHCl_3$); $^1H$ NMR (500 MHz, $CDCl_3$+ TMS) δ 4.09 (1H, s, 8α-H), 4.07 (1H, dd, J=10.7, 3.5 Hz, 22-H), 3.78 (1H, dd, J=10.7, 7.5 Hz, 22-H), 2.05 (3H, s, CO Me), 1.99 (1H, dm, J=12.8 Hz), 1.00 (3H, d, J=6.6 Hz, 21-$H_3$), 0.96 (3H, s, 18-$H_3$); $^{13}C$ NMR (125 MHz) δ 171.35 (s, C=O), 69.39 (t, C-22), 69.07 (d, C-8), 53.21 (d), 52.30 (d), 41.91 (s, C-13), 40.19 (t), 35.30 (d), 33.54 (t), 26.60 (t), 22.53 (t), 20.95 (q, COMe), 17.36 (t), 16.97 (q, C-21), 13.50 (q, C-18); MS (EI) m/z 254 (10, M$^+$), 236 (24, M$^+$-$H_2O$), 212 (9, M$^+$-$C_2H_2O$), 194 (67, M$^+$-$CH_3COOH$), 176 (91, M$^+$-$CH_3COOH$—$H_2O$), 161 (83), 150 (80), 135 (91), 125 (97), 112 (98), 97 (100); exact mass calculated for $C_{15}H_{24}O_2$ (M$^+$-$H_2O$) 235.1776. found 236.1771.

Preparation of (8S,20S)-de-A,B-8-triethylsilyloxy-20-(acetyloxymethyl)-pregnane (3)

Triethylsilyl trifluoromethanesulfonate (1.9 mL, 2.24 g, 8.5 mmol) was added to a solution of the alcohol 2 (2.08 g, 8.2 mmol) and 2,6-lutidine (2.86 mL, 2.63 g, 24.6 mmol) in anhydrous dichloromethane (10 mL) at 0° C. The mixture was stirred under argon at 0° C. for 0.5 h. The reaction was quenched with water (30 mL) and extracted with dichloromethane. The combined organic phase washed with water, dried ($Na_2SO_4$) and concentrated under reduced pressure. The product 3 (2.9 g, 96% yield) was isolated by a chromatography on silica gel with hexane/ethyl acetate (95:5), as a colorless oil:

$[\alpha]_D$+40.8° (c 1.95, $CHCl_3$); $^1H$ NMR (400 MHz, $CDCl_3$) δ 4.06 (1H, dd, J=10.7, 3.4 Hz, 22-H), 4.04 (1H, s, 8α-H), 3.77 (1H, dd, J=10.7, 7.6 Hz, 22-H), 2.04 (3H, s, COMe), 1.93 (1H, dm, J=12.4 Hz), 0.98 (3H, d, J=6.6 Hz, 21-$H_3$), 0.94 (9H, t, J=7.9 Hz, Si($CH_2CH_3$)$_3$), 0.92 (3H, s, 18-$H_3$), 0.55 (6H, q, J=7.9 Hz, Si(C $CH_2CH_3$)$_3$); $^{13}C$ NMR (100 MHz) δ 171.39 (s, C=O), 69.57 (t, C-22), 69.22 (d, C-8), 53.41 (d), 52.81 (d), 42.22 (s, C-13), 40.60 (t), 35.36 (d), 34.59 (t), 26.77 (t), 23.04 (t), 20.99 (q, COMe), 17.64 (t), 17.05 (q, C-21), 13.53 (q, C-18), 6.92 (q, Si$CH_2CH_3$), 4.93 (t, Si$CH_2CH_3$); MS (EI) m/z 368 (29, M$^+$), 339 (85, M$^+$-$C_2H_5$), 325 (78, M$^+$-$CH_3CO$), 265 (31, M$^+$-$CH_3COOC_3H_7$—H), 237 (21, M$^+$-$Et_3SiO$), 217 (88), 189 (72), 177 (92), 161 (77), 145 (93), 135 (98), 121 (90), 107 (91), 95 (100); exact mass calculated for $C_{19}H_3SO_3Si$ (M$^+$-$C_2H_5$) 339.2355. found 339.2352.

Preparation of (8S,20S)-de-A,B-8-triethylsilyloxy-20-(hydroxymethyl)-pregnane (4)

A solution of sodium hydroxide (1.5 g, 37.5 mmol) in anhydrous ethanol (20 mL) was added to a mixture of the compound 3 (2.9 g, 7.9 mmol) in anhydrous ethanol (10 mL). The reaction mixture was stirred at room temperature for 30 min. and then neutralized with 5% aq. hydrochloric acid. The mixture was extracted with dichloromethane and the combined organic phases were washed with water, dried ($Na_2SO_4$) and concentrated under reduced pressure. The residue was chromatographed on silica gel with hexane/ethyl acetate (95:5, then 9:1) to give the alcohol 4 (2.58 g, 100% yield):

$[\alpha]_D$+38.9° (c 2.45, $CHCl_3$); $^1H$ NMR (500 MHz, $CDCl_3$) δ 4.07 (1H, d, J=2.3 Hz, 8α-H), 3.66 (1H, dd, J=10.5, 3.2, Hz, 22-H), 3.39 (1H, dd, J=10.5, 6.8 Hz, 22-H), 1.98 (1H, dm, J=12.7 Hz), 1.05 (3H, d, J=6.6 Hz, 21-$H_3$), 0.98 (9H, t, J=7.9 Hz, Si($CH_2CH_3$)$_3$), 0.95 (3H, s, 18-$H_3$), 0.58 (6H, q, J=7.9 Hz, Si($CH_2CH_3$)$_3$); $^{13}C$ NMR (125 MHz) δ 69.26 (d, C-8), 67.97 (t, C-22), 53.10 (d), 52.86 (d), 42.14 (s, C-13), 40.63 (t), 38.28 (d), 34.60 (t), 26.80 (t), 23.05 (t), 17.64 (t), 16.65 (q, C-21), 13.56 (q, C-18), 6.91 (q, Si$CH_2CH_3$), 4.92 (t, Si $CH_2CH_3$); MS (EI) m/z 326 (58, M$^+$), 311 (15, M$^+$-$CH_3$), 297 (93, M$^+$-$C_2H_5$), 283 (89, M$^+$-$C_2H_2O$), 225 (80), 211 (24, M$^+$-$Et_3Si$), 193 (90), 177 (98), 135 (98), 121 (99), 107 (99), 95 (100); exact mass calculated for $C_{19}H_{38}O_2Si$ (M$^+$) 326.2641. found 326.2549.

Preparation of (8S,20S)-de-A,B-8-triethylsilyloxy-20-(iodomethyl)-pregnane (5)

A solution of iodine (1.52 g, 6 mmol) in methylene chloride (120 mL) was slowly added to a solution of triphenylphosphine (1.6 g, 6.1 mmol) and imidazole (816 mg, 12 mmol) in methylene chloride (10 mL) at 0° C. After 15 min. a solution of alcohol 4 (0.5 g, 1.5 mmol) in methylene chloride (10 mL) was added, the mixture was stirred at 0° C. for 20 min. and at room temperature for 18 h. The reaction mixture washed with water, dried ($Na_2SO_4$) and concentrated under reduced pressure. The residue was chromatographed on silica gel with hexane to give the desired iodide 5 (657 mg, 100%):

$[\alpha]_D$+52.0° (c 1.44, $CHCl_3$); $^1$H NMR (400 MHz, $CDCl_3$) δ 4.04 (1H, d, J=2.1 Hz, 8α-H), 3.33 (1H, dd, J=9.5, 2.3 Hz, 22-H), 3.17 (1H, dd, J=9.5, 5.3 Hz), 1.90 (1H, dm, J=12.5 Hz), 0.99 (3H, d, J=5.9 Hz, 21-$H_3$), 0.95 (9H, t, J=7.9 Hz, Si($CH_2CH_3$)$_3$), 0.95 (3H, s, 18-$H_3$), 0.55 (6H, q, J=7.9 Hz, Si($CH_2CH_3$)$_3$); $^{13}$C NMR (100 MHz) δ 69.25 (d, C-8), 56.03 (d), 52.80 (d), 42.10 (s, C-13), 40.46 (t), 36.46 (d), 34.50 (t), 26.66 (t), 22.85 (t), 21.61 (t), 20.71 (q, C-21), 17.61 (t), 14.34 (q, C-18), 6.94 (q, Si$CH_2CH_3$), 4.93 (t, Si$CH_2CH_3$); MS (EI) m/z 436 (42, M$^+$), 421 (3, M$^+$-$CH_3$), 407 (95, M$^+$-$C_2H_9$), 393 (76), 309 (23, M$^+$-I), 303 (86, M$^+$-$Et_3$SiOH—H), 251 (28), 225 (35), 177 (96), 135 (96), 121 (87), 95 (97), 75 (100); exact mass calculated for $C_{19}H_{37}$OSiI (M$^+$) 436.1658. found 436.1645.

Preparation of (8S,20R)-de-A,B-8-triethylsilyloxy-20-(3-isopropoxycarbonyl)-propyl-pregnane (6)

A mixture of zinc powder (488 mg, 7.5 mmol), anhydrous pyridine (8 mL) and isopropyl acrylate (900 µL, 855 mg, 7.5 mmol) was warmed to 50° C., then nickel (II) chloride hexahydrate (428 mg, 1.8 mmol) was added. The resulting mixture was warmed to 65° C. and stirred for 2 h until its green color turned to reddish brown one. After cooling to 0° C., a solution of iodide 5 (657 mg, 1.5 mmol) in anhydrous pyridine (6 mL) was added and the reaction mixture was stirred for 7 h at room temperature. The mixture was diluted with ethyl acetate (20 mL) and the resulting precipitate was filtered off through a pad of Celite. The filtrate washed with 5% aq. HCl and brine, dried ($Na_2SO_4$) and concentrated under reduced pressure. The residue was chromatographed on silica gel with hexane and hexane/ethyl acetate (95:5) to give the ester 6 (494 mg, 78%): $[\alpha]_D$+41.8° (c 1.41, $CHCl_3$); $^1$H NMR (500 MHz, $CDCl_3$) δ 4.99 (1H, sep, J=6.3 Hz, OCH$Me_2$), 4.01 (1H, s, 8α-H), 2.22 (2H, m, 24-$H_2$), 1.93 (1H, dm, J=12.2 Hz), 1.22 (6H, d, J=6.3 Hz, OCH$Me_2$), 0.93 (9H, t, J=7.9 Hz, Si(CH$CH_3$)$_3$), 0.89 (3H, d, J=5.6 Hz, 21-$H_3$), 0.88 (3H, s, 18-$H_3$), 0.54 (6H, q, J=7.9 Hz, Si($CH_2CH_3$)$_3$); $^{13}$C NMR (125 MHz) δ 173.44 (s, COO-iPr), 69.37 (d, C-8), 67.26 (d, COOCH$Me_2$), 56.50 (d), 53.06 (d), 42.09 (s, C-13), 40.74 (t), 35.20 (t), 35.13 (t), 35.01 (d), 34.63 (t), 27.25 (t), 22.98 (t), 21.84 (q, COOCH$Me_2$), 21.58 (t), 18.52 (q, C-21), 17.66 (t), 13.46 (q, C-18), 6.92 (q, Si$CH_2CH_3$), 4.91 (t, Si$CH_2CH_3$); MS (EI) m/z 424 (35, M$^+$), 409 (6, M$^+$-$CH_3$), 395 (87, M$^+$-$C_2H_9$), 381 (39, M$^+$-$C_3H_7$), 365 (41, M$^+$-$C_3H_7$O), 335 (90, M$^+$-$C_3H_7$COOH—H), 295 (29), 249 (26), 225 (64), 215 (54), 199 (33), 171 (29), 135 (88), 115 (55), 103 (100); exact mass calculated for $C_{25}H_{48}O_3$Si (M$^+$) 424.3373. found 424.3373.

Preparation of (8S,20R)-de-A,B-8-triethylsilyloxy-20-(4-hydroxy-butyl)-pregnane (7)

Lithium aluminium hydride (19 mg, 0.5 mmol) was added to a solution of ester 6 (100 mg, 0.24 mmol) in anhydrous THF (8 mL) at 0° C. A cooling bath was removed and the reaction mixture was stirred for 18 h at room temperature. The excess hydride was quenched by careful, successive addition of methanol. A saturated aq. solution of the tartaric acid was added and the mixture was extracted with methylene chloride. The combined organic phase washed with water, dried ($Na_2SO_4$) and concentrated under reduced pressure. The residue was chromatographed on silica gel with hexane/ethyl acetate (95:5) to give the alcohol 7 (87 mg, 99%):

$[\alpha]_D$+46.7° (c 0.78, $CHCl_3$); $^1$H NMR (500 MHz, $CDCl_3$) δ 4.02 (1H, d, J=2.0 Hz, 8α-H), 3.63 (2H, t, J=6.6 Hz, 25-$H_2$), 1.95 (1H, dm, J=12.6 Hz), 0.95 (9H, t, J=7.9 Hz, Si($CH_2CH_3$)$_3$), 0.90 (3H, s, 18-$H_3$), 0.89 (3H, d, J=7.9 Hz, 21-$H_3$), 0.55 (6H, q, J=7.9 Hz, Si($CH_2CH_3$)$_3$); $^{13}$C NMR (125 MHz) δ 69.38 (d, C-8), 63.07 (t, C-25), 56.68 (d), 53.08 (d), 42.09 (s, C-13), 40.77 (t), 35.54 (t), 35.20 (d), 34.63 (t), 33.26 (t), 27.29 (t), 22.98 (t), 22.17 (t), 18.53 (q, C-21), 17.67 (t), 13.47 (q, C-18), 6.91 (q, Si$CH_2CH_3$), 4.91 (t, Si$CH_2CH_3$); MS (EI) m/z 368 (8, M$^+$), 353 (4, M$^+$-$CH_3$), 339 (56, M$^+$-$C_2H_7$), 325 (53), 297 (18), 283 (13), 225 (54), 177 (37), 163 (69), 135 (93), 103 (100); exact mass calculated for $C_{20}H_{39}O_2$Si (M$^+$-$C_2H_5$) 399.2719. found 339.2713.

Preparation of (8S,20R)-de-A,B-20-(4-hydroxy-butyl)-pregnan-8-ol (8)

To a solution of compound 7 (86 mg, 0.23 mmol) in tetrahydrofuran (2 mL) and acetonitrile (2 mL) a mixture of aq. 48% HF/acetonitrile (1:9 ratio, 2 mL) was added at 0° C. and the resulting mixture was stirred at room temperature for 1 h. Saturated aq. $NaHCO_3$ solution was added and the reaction mixture was extracted with ethyl acetate. The combined organic phase washed with brine, dried ($Na_2SO_4$) and concentrated under reduced pressure. The residue was chromatographed on silica gel with hexane/ethyl acetate (9:1) to give the diol 8 (60 mg, 100%):

$[\alpha]_D$+40.2° (c 3.05, $CHCl_3$); $^1$H NMR (500 MHz, $CDCl_3$) δ 4.06 (1H, d, J=2.3 Hz, 8α-H), 3.62 (2H, t, J=6.6 Hz, 25-$H_2$), 1.99 (1H, dm, J=13.0 Hz), 0.92 (3H, s, 18-$H_3$), 0.90 (3H, d, J=6.5 Hz, 21-$H_3$); $^{13}$C NMR (125 MHz) δ 69.28 (d, C-8), 62.89 (t, C-25), 56.47 (d), 52.53 (d), 41.75 (s, C-13), 40.30 (t), 35.45 (t), 35.14 (d), 33.46 (t), 33.16 (t), 27.10 (t), 22.44 (t), 22.13 (t), 18.42 (q, C-21), 17.36 (t), 13.43 (q, C-18); MS (EI) m/z 254 (7, M$^+$), 236 (8, M$^+$-$H_2$O), 221 (7, M$^+$-$H_2$O—$CH_3$), 163 (8, M$^+$-$H_2$O—$C_4H_8$OH), 135 (25, M$^+$-$H_2$O—$C_6H_{12}$OH), 125 (35), 111 (100), 97 (30); exact mass calculated for $C_{16}H_{30}$O (M$^+$) 254.2246. found 254.2450.

Preparation of (8S,20R)-de-A,B-20-[4-(tert-butyldimethylsilyloxy)-butyl]-pregnan-8-ol (9)

tert-butyldimethylsilyl chloride (47 mg, 0.31 mmol) was added to a solution of the diol 8 (60 mg, 0.23 mmol) and triethylamine (134 µL, 97 mg, 0.96 mmol) in anhydrous methylene chloride (4 mL). The mixture was stirred under argon at room temperature for 18 h. The reaction was quenched with water and extracted with ethyl acetate. The combined organic phase washed with brine, dried ($Na_2SO_4$) and concentrated under reduced pressure. The residue was chromatographed on silica gel with hexane and hexane/ethyl acetate (98:2) to give the alcohol 9 (84 mg, 100%):

$[\alpha]_D$+30.1° (c 3.8, $CHCl_3$); $^1$H NMR (500 MHz, $CDCl_3$) δ 4.05 (1H, d, J=2.2 Hz, 8α-H), 3.58 (2H, t, J=6.6 Hz, 25-$H_2$), 1.98 (1H, dm, J=12.8 Hz), 0.92 (3H, s, 18-$H_3$), 0.88 (3H, d, 21-$H_3$) covered by 0.88 (9H, s, Si-t-Bu), 0.04 (6H, s, Si$Me_2$); $^{13}$C NMR (125 MHz) δ 69.36 (d, C-8), 63.24 (t, C-25), 56.65 (d), 52.60 (d), 41.82 (s, C-13), 40.38 (t), 35.46 (t), 35.20 (d), 33.57 (t), 33.29 (t), 27.13 (t), 25.95 (q, Si$CMe_3$), 22.49 (t), 22.16 (t), 18.44 (q, C-21), 18.33 (s, Si$CMe_3$), 17.41 (t), 13.49

(q, C-18), −5.28 (q, SiMe$_2$); MS (EI) m/z no M$^+$, 311 (1, M$^+$-C$_4$H$_9$), 293 (3, $\overline{M^+}$-C$_4$H$_9$—H$_2$O), 251 (9, M$^+$-t-BuSiMe$_2$H—H), 219 (32, M$^+$-H$_2$O— t-BuSiMe$_2$O), 163 (54), 149 (30), 135 (55), 123 (63), 109 (100), 95 (76); exact mass calculated for C$_{18}$H$_{35}$O$_2$Si (M$^+$-C$_4$H$_9$) 311.2406. found 311.2399.

Preparation of (20R)-de-A,B-20-[4-(tert-butyldimethylsilyloxy)-butyl]-pregnan-8-one (10)

Pyridinium dichromate (127 mg, 0.34 mmol) was added to a solution of the alcohol 9 (26 mg, 71 □mol) and pyridinium p-toluenesulfonate (3 mg, 12 □mol) in anhydrous methylene chloride (6 mL). The resulting suspension was stirred at room temperature for 3 h. The reaction mixture was filtered through a Waters silica Sep-Pak cartridge (5 g) that was further washed with methylene chloride. After removal of solvents the ketone 10 (23 mg, 89% yield) was obtained as a colorless oil:

[α]$_D$+3.8° (c 1.5, CHCl$_3$); $^1$H NMR (400 MHz, CDCl$_3$) δ 3.59 (2H, t, J=6.4 Hz, 25-H$_2$), 2.43 (1H, dd, J=11.6, 7.5 Hz), 0.94 (3H, d, J=6.1 Hz, 21-H$_3$), 0.885 (9H, s, Si-t-Bu), 0.626 (3H, s, 18-H$_3$), 0.039 (6H, s, SiMe$_2$); $^{13}$C NMR (100 MHz) δ 212.14 (s, C-8), 63.16 (t, C-25), 61.97 (d), 56.65 (d), 49.90 (s, C-13), 40.95 (t), 38.96 (t), 35.43 (d and t), 33.20 (t), 27.48 (t), 25.95 (q, SiCMe$_3$), 24.05 (t), 22.16 (t), 19.03 (t), 18.62 (q, C-21), 18.33 ($\overline{s, SiCMe_3}$), 12.45 (q, C-18), −5.27 (q, SiMe$_2$); MS (EI) m/z 367 (1, M$^+$+H), 351 (2, M$^+$-CH$_3$), 309 (66, M$^+$-C$_4$H$_9$), 267 (17), 217 (39, M$^+$-H$_2$O-t-BuSiMe$_2$O), 175 (21), 161 (34), 135 (92), 121 (51), 95 (49), 75 (100); exact mass calculated for C$_{18}$H$_{33}$O$_2$Si (M$^+$-C$_4$H$_9$) 309.2250. found 309.2244.

Preparation of (20R)-2-methylene-19,26,27-trinor-1α,25-dihydroxycalciferol (13)

To a solution of phosphine oxide 11 (87 mg, 149 μmol) in anhydrous THF (600 μL) at −20° C. was slowly added PhLi (1.3 M in cyclohexane-ether, 200 μL, 260 μmol) under argon with stirring. The solution turned deep orange. After 30 min the mixture was cooled to −78° C. and a precooled (−78° C.) solution of ketone 10 (18 mg, 49 μmol) in anhydrous THF (200 μL) was slowly added. The mixture was stirred under argon at −78 □C for 3 h and at 0° C. for 18 h. Ethyl acetate was added, and the organic phase washed with brine, dried (Na$_2$SO$_4$) and evaporated. The residue was dissolved in hexane and applied on a Waters silica Sep-Pak cartridge (2 g). The cartridge washed with hexane and hexane/ethyl acetate (99.5:0.5) to give 19-norvitamin derivative 12 (32 mg). The Sep-Pak was then washed with hexane/ethyl:acetate (96:4) to recover the unchanged C,D-ring ketone 10 (5 mg, 14 μmol), and with ethyl acetate to recover diphenylphosphine oxide 11(55 mg). The protected vitamin 12 was further purified by HPLC (9.4×250 mm Zorbax Sil column, 4 mL/min) using hexane/2-propanol (99.9:0.1) solvent system. Pure compound 12 (31.55 mg, 88% yield) was eluted at R$_f$=4.09 min as a colorless oil:

UV (in hexane) λ$_{max}$ 262.3, 252.0, 243.6 nm; $^1$H NMR (500 MHz, CDCl$_3$) δ 6.22 and 5.84 (each 1H, each d, J=11.1 Hz, 6- and 7-H), 4.97 and 4.92 (each 1H, each s, =CH$_2$), 4.42 (2H, m, 1β- and 3α-H), 3.61 (2H, t, J=6.5 Hz, 25-H$_2$), 2.82 (1H, dm, J=12.1 Hz, 9β-H), 2.52 (1H, dd, J=13.3, 5.9 Hz, 10α-H), 2.46 (1H, dd, J=12.6, 4.4 Hz, 4α-H), 2.33 (1H, dm, J=13.3 Hz, 110-H), 2.18 (1H, dd, J=12.6, 8.3 Hz, 4, —H), 1.99 (2H, m), 0.92 (3H, d, J=6.4 Hz, 21-H$_3$), 0.902 (9H, s, Si-t-Bu), 0.899 (9H, s, Si-t-Bu), 0.867 (9H, s, Si-t-Bu), 0.545 (3H, s, 18-H$_3$), 0.082 (3H, s, SiMe), 0.069 (3H, s, SiMe), 0.056 (6H, s, 2×SiMe), 0.052 (3H, s, SiMe), 0.028 (3H, s, SiMe); $^{13}$C NMR (125 MHz) δ 152.99 (s, C-2), 141.26 (s, C-8), 132.70 (s, C-5), 122.43 (d, C-6), 116.10 (d, C-7), 106.25 (t, =CH$_2$), 72.54 and 71.63 (each d, C-1 and C-3), 63.31 (t, C-25), 56.58 (d), 56.29 (d), 47.62 (t), 45.68 (s, C-13), 40.61 (t), 38.56 (t), 36.09 (t), 35.64 (t), 33.32 (t), 28.76 (t), 27.71 (t), 25.99 (q, SiCMe$_3$), 25.84 (q, SiCMe$_3$), 25.78 (q, SiCMe$_3$), 23.45 (t), 22.$\overline{28}$ (t), 22.22 (t), 18.$\overline{76}$ (q, C-21), 18.38 $\overline{(s, Si}$ CMe$_3$), 18.25 (s, SiCMe$_3$), 18.16 (s, SiCMe$_3$), 12.06 (q, $\overline{C}$-18), −4.86 and −5.$\overline{09}$ and −5.23 (each q, $\overline{6}$×SiMe); MS (EI) m/z no M$^+$, 673 (8, M$^+$-C$_4$H$_9$), 628 (2, M$^+$-t Bu$\overline{Me}$SiH$_2$), 598 (100, M$^+$-t-BuMe$_2$SiOH), 556 (9), 541 (4), 496 (3), 366 (42), 257 (10), 234 (13), 147 (20); exact mass calculated for C$_{43}$H$_{82}$O$_3$Si$_3$Na (MNa$^+$) 753.5470. found 753.5474.

Protected vitamin 12 (31.54 mg, 43 μmol) was dissolved in THF (3 mL) and acetonitrile (3 mL). A solution of aq. 48% HF in acetonitrile (1:9 ratio, 2 mL) was added at 0° C. and the resulting mixture was stirred at room temperature for 3 h. Saturated aq. NaHCO$_3$ solution was added and the reaction mixture was extracted with ethyl acetate. The combined organic phase washed with brine, dried (Na$_2$SO$_4$) and concentrated under reduced pressure. The residue was diluted with 2 mL of hexane/ethyl acetate (8:2) and applied on a Waters silica Sep-Pak cartridge (2 g). An elution with hexane/ethyl acetate (8:2) and ethyl acetate gave the crude product 13 (20 mg). The vitamin 13 was further purified by straight phase HPLC [9.4×250 mm Zorbax Sil column, 5 mL/min, hexane/2-propanol (85:15) solvent system, R$_f$=8.75 min.] and later by reverse phase HPLC [9.4×250 mm Zorbax Eclipse XDB-C18 column, 4 mL/min, methanol/water (85:15) solvent system, R$_f$=7.90 min.] to give a colorless oil (13.15 mg, 79% yield):

UV (in EtOH) λ$_{max}$ 262.2, 252.7, 244.2 nm; $^1$H NMR (500 MHz, CDCl$_3$) δ 6.34 and 5.88 (1H and 1H, each d, J=11.1 Hz, 6- and 7-H), 5.10 and 5.08 (each 1H, each s, =CH$_2$), 4.46 (2H, m, 1β- and 3α-H), 3.64 (2H, dd, J=11.8, 6.1 Hz, 25-H$_2$), 2.84 (1H, dd, J=13.1, 4.3 Hz, 10p-H), 2.81 (1H, br d, J=15.2 Hz, 9β-H), 2.56 (1H, dd, J=13.3, 3.0 Hz, 4α-H), 2.32 (1H, dd, J=13.3, 6.0 Hz, 4β-H), 2.27 (1H, dd, J=13.1, 8.5 Hz, 10α-H), 0.92 (3H, d, J=6.3 Hz, 21-H$_3$), 0.542 (3H, s, 18-H$_3$); $^{13}$C NMR (125 MHz) δ 151.95 (s, C-2), 143.37 (s, C-8), 130.42 (s, C-5), 124.19 (d, C-6), 115.28 (d, C-7), 107.70 (t, =CH$_2$), 71.79 and 70.61 (each d, C-1 and C-3), 63.08 (t, C-25), 56.40 (d), 56.30 (d), 45.75 (s, C-13) covered by 45.75 (t), 40.42 (t), 38.13 (t), 36.02 (d), 35.63 (t), 33.23 (t), 28.94 (t), 27.63 (t), 23.47 (t), 22.25 (t), 22.20 (t), 18.75 (q, C-21), 12.06 (q, C-18); MS (EI) m/z 388(3, M$^+$), 334(1, M$^+$-3H$_2$O), 318 (9, M$^+$-3H$_2$O—CH$_4$), 272 (9), 252 (27), 250 (28), 239 (8), 196 (99), 194 (100), 160 (12); exact mass calculated for C$_{25}$H$_{40}$O$_3$ (M$^+$) 388.2977. found 388.2961.

Preparation of (20R)-2α-methyl-19,26,27-trinor-1α,25-dihydroxycalciferol (14) and (20R)-2β-methyl-19,26,27-trinor-1α,25-dihydroxycalciferol (15)

Tris(triphenylphosphine)rhodium (I) chloride (7 mg, 7.6 μmol) was added to dry benzene (5 mL) presaturated with hydrogen (15 min.). The mixture was stirred at room temperature until a homogeneous solution was formed (25 min). A solution of vitamin 13 (2.9 mg, 7.5 μmol) in dry benzene (3 mL) was then added and the reaction was allowed to proceed under a continuous stream of hydrogen for 4 h. Benzene was removed under vacuum, the residue was redissolved in hexane/ethyl:acetate (1:1) and applied on a Waters silica Sep-Pak cartridge (2 g). A mixture of 2-methyl vitamins was eluted with the same solvent system. The compounds were further purified by HPLC (9.4×250 mm Zorbax-Sil column, 5 mL/min) using hexane/2-propanol (85:15) solvent system. The mixture of 2-methyl-19-norvitamins 14 and 15 gave a single peak at R$_f$=8.91 min. Separation of both epimers was achieved by reversed-phase HPLC (9.4×250 mm Zorbax Eclipse XDB-C18 column, 3 mL/min) using methanol/water (85:15) solvent system. 2β-Methyl vitamin 15 (911 μg, 31% yield) was collected at $R_t$=8.71 min. and its 2α-epimer 14 (1.055 μg, 36% yield) at $R_t$=9.27 min:

2α-Methyl analog 14: UV (in EtOH) $\lambda_{max}$ 260.5, 251.5, 243.5 nm; $^1$H NMR (500 MHz, CDCl$_3$) δ 6.37 and 5.82 (1H and 1H, each d, J=11.1 Hz, 6- and 7-H), 3.96 (1H, m, 1β-H), 3.63 (3H, m, 3α-H and 25-H$_2$), 2.80 (2H, br m, 9β- and 10α-H), 2.60 (1H, dd, J=12.8, 4.4 Hz, 4α-H), 2.22 (1H, br d, J=14.3 Hz, 10β-H), 2.13 (1H, ~t, J~11.3 Hz, 4β-H), 1.132 (3H, d, J=6.8 Hz, 2α-CH$_3$), 0.926 (3H, d, J=6.5 Hz, 21-H$_3$), 0.531 (3H, s, 18-H$_3$); MS (EI) m/z 390 (100, M$^+$), 372 (14, M$^+$-H$_2$O), 357 (4, M$^+$-H$_2$O—CH$_3$), 339 (3, M$^+$-2H$_2$O—CH$_3$), 317 (23, M$^+$-C$_4$H$_8$OH), 289 (76, M$^+$-C$_6$H$_{12}$OH), 271 (45, M$^+$-C$_6$H$_{12}$OH—H$_2$O), 253 (40), 235 (46), 194 (35), 159 (30), 147 (57), 135 (70); exact mass calculated for C$_{25}$H$_{42}$O$_3$ (M$^+$) 390.3134. found 390.3121.

2□-Methyl analog 15: UV (in EtOH) $\lambda_{max}$ 260.5, 251.0, 243.5 nm; $^1$H NMR (500 MHz, CDCl$_3$) δ 6.26 and 5.87 (1H and 1H, each d, J=11.2 Hz, 6-H and 7-H), 3.90 (1H, m, 3α-H), 3.65 (2H, dd, J=12.2, 6.4 Hz, 25-H$_2$), 3.50 (1H, m, 1β-H), 3.08 (1H, dd, J 12.9, 4.1 Hz, 10β-H), 2.79 (1H, dd, J=12.2, 4.3 Hz, 9βH), 2.43 (1H, br d, J=ca. 13.7 Hz, 4α-H), 2.34 (1H, dd, J=13.7, 2.6 Hz, 4β-H), 1.142 (3H, d, J=6.8 Hz, 2β-CH$_3$), 0.930 (3H, d, J=6.4 Hz, 21-H$_3$), 0.543 (3H, s, 18-H$_3$); MS (EI) m/z 390 (100, M$^+$), 372 (17, M$^+$-H$_2$O), 354(5 μM$^+$-2H$_2$O), 339(3 μM$^+$-2H$_2$O—CH$_3$), 317 (21, M$^+$-C$_4$H$_8$OH), 289 (62, M$^+$-C$_6$H$_{12}$OH), 271 (37, M$^+$-C$_6$H$_{12}$OH—H$_2$O), 253 (39), 247 (33), 235 (46), 194 (32), 159 (29), 147 (53), 135 (71); exact mass calculated for C$_{25}$H$_{42}$O$_3$ (M$^+$) 390.3134. found 390.3133.

Example II

Biological Activity

Experimental Methods:
(A) Vitamin D Receptor Binding
Test Material
Protein Source Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand (3H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

(B) HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

(C) In vitro Transcription Assay

Transcription activity was measured in ROS 17/2.8 (bone) cells that were stably transfected with a 24-hydroxylase (24 Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units (D) Intestinal Calcium Transport and Bone Calcium Mobilization Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Figure 2:
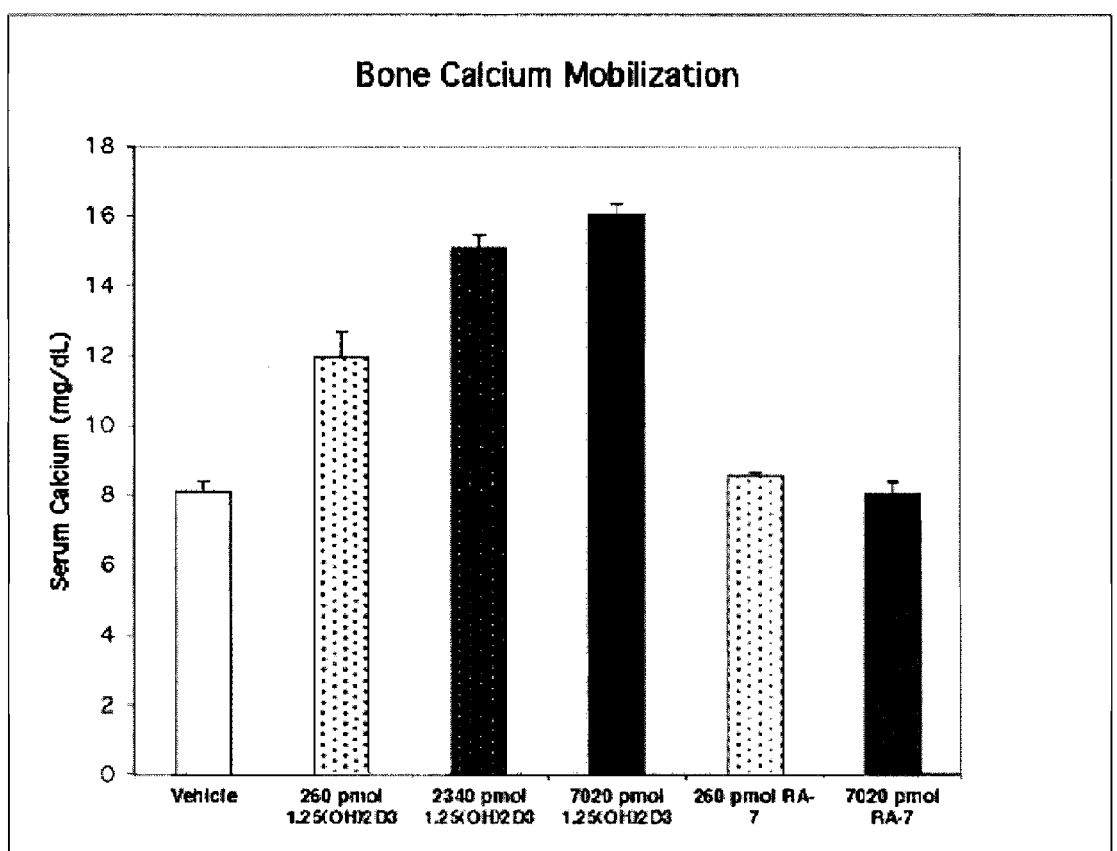
Figure 3:
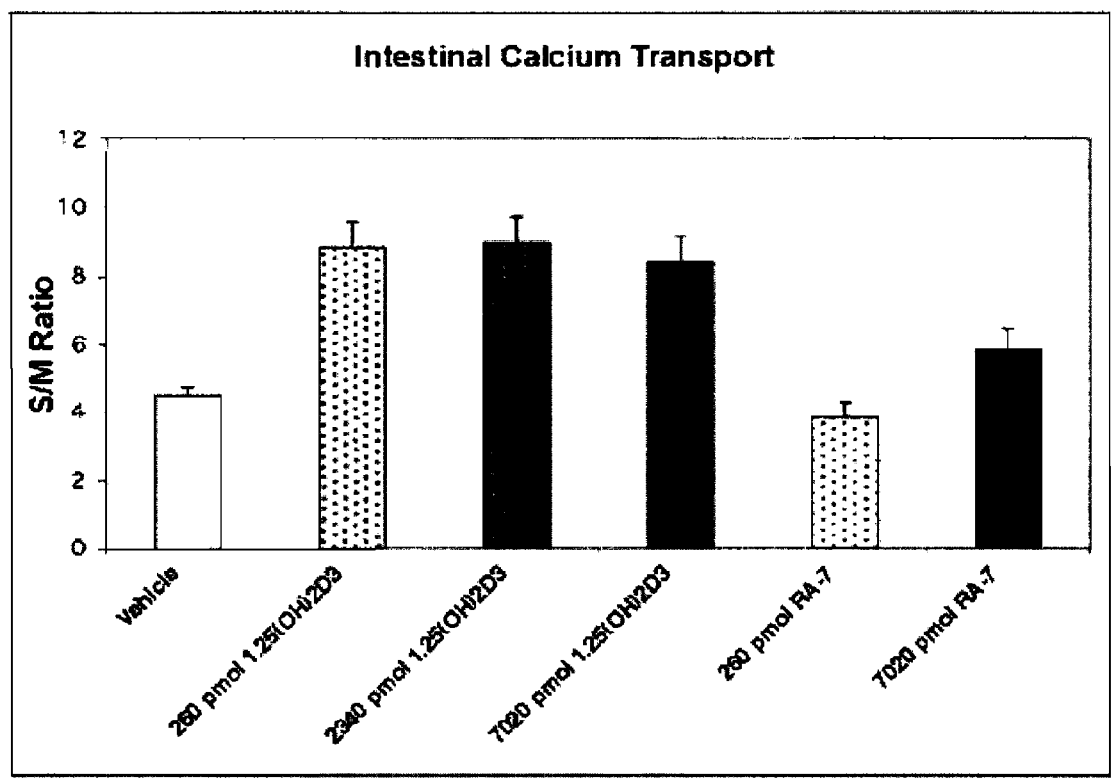
Figure 4:
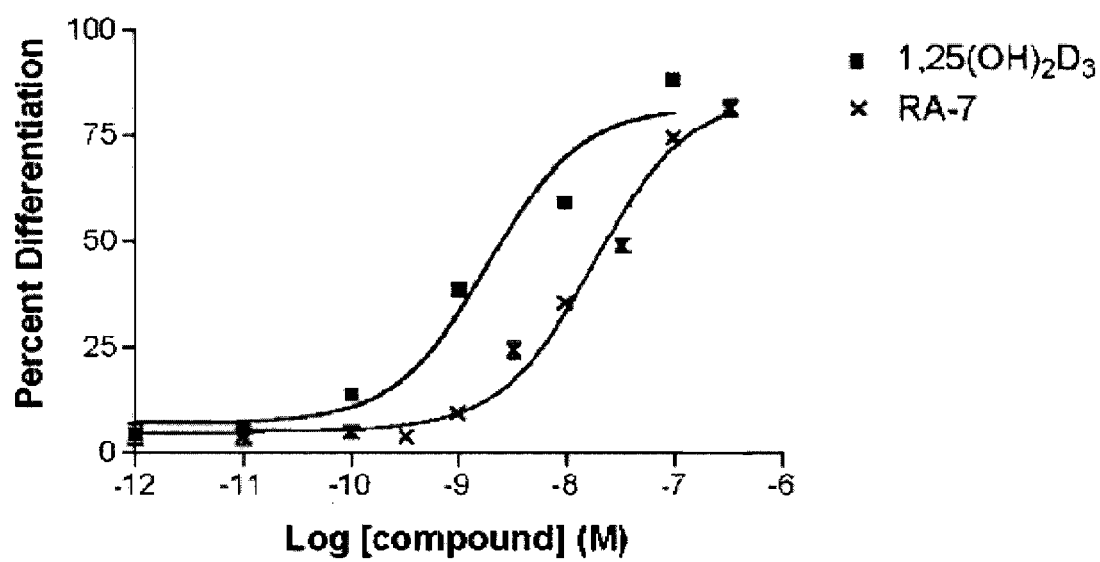
Figure 5:
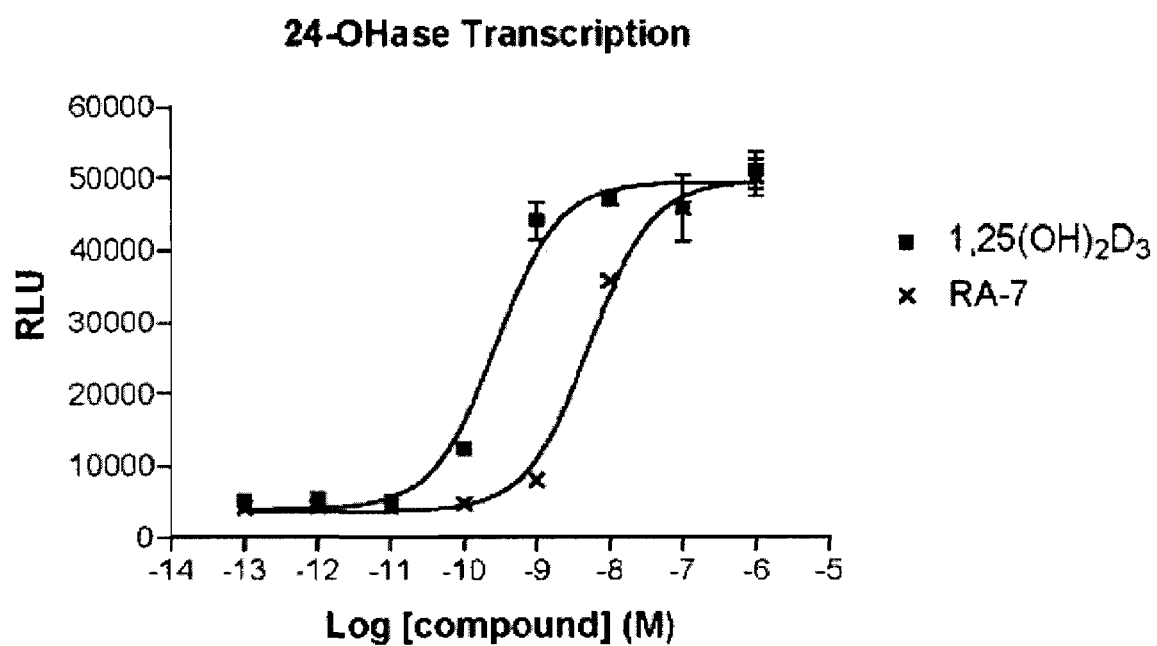

RA-7 binds to the vitamin D receptor (VDR) but not as well as the native hormone 1α,25-dihydroxyvitamin D$_3$ (see FIG. 1). It is about one-tenth as active as the native hormone in binding to and presumably in activating the receptor. Additionally, it is less active in stimulating transcription of a reporter gene stably transfected in Ros17/2.8 (bone) cells, indicating a lesser biological activity as 1α,25-dihydroxyvitamin D$_3$ (see FIG. 5). It is also active in inhibiting the proliferation and causing the differentiation of the cancerous HL-60 cell. (see FIG. 4) However, even when dosed at 30 times the native hormone or 7,020 pmol per day, it was unable to cause the mobilization of calcium from bone (see FIG. 2). It furthermore has virtually no activity in raising the intestinal calcium transport activity even when given at 30 times that of the native hormone (see FIG. 3). Accordingly, this compound should be effective in treating secondary hyperparathyroidism of renal failure without raising serum calcium. Further, RA-7 is expected to possess significant activity in suppressing parathyroid hormone levels in normal rats. It should also be very active in the treatment of colon, breast, skin, lung and prostate cancer without elevating calcium and inducing vitamin D intoxication. It may also be useful in the treatment of multiple sclerosis or inflammatory bowel diseases, such as celiac disease, ulcerative colitis and Crohn's disease.

Similarly, other similar compounds of the present invention as shown in formula IA, IIA and IIIA, are expected to bind to the vitamin D receptor, stimulate transcription of a reporter gene stably transfected in Ros 17/2.8 (bone) cells, induce differentiation of HL-60 cells, have limited calcemic activity when measured either by intestinal calcium transport or bone calcium mobilization than 1α,25-dihydroxyvitamin $D_3$ and possess significant activity in suppressing parathyroid hormone levels in normal rats.

Accordingly, this compound RA-7 and other compounds described in the invention should find its uses in the treatment of autoimmune diseases such as multiple sclerosis, type I diabetes, rheumatoid arthritis, lupus, and other similar degenerative diseases. It should also have significant activity in treating malignant growth such as colorectal, breast, skin, lung and prostate cancers. All of these activities should be evident in the absence of raising serum calcium concentrations (see FIGS. 2 and 3). This compound should also be useful in treating secondary hyperparathyroidism found in patients who have lost kidney function such as those on hemodialysis or peritoneal dialysis.

In one embodiment, the compound of formula IA IIA or IIIA is used in a pharmaceutical composition. For example, each ml of the pharmaceutical composition may comprise 5 µg of the compound, 30% (v/v) propylene glycol and 20% (v/v) alcohol.

The compounds of the invention are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and or reducing body fat in animal subject includes administering to the animal subject, an effective amount of the compound or a pharmaceutical composition that includes the compound. Administration of the compound or the pharmaceutical composition to the subject inhibits adipocyte differentiation, inhibits gene transcription, and/or reduces body fat in the animal subject.

For treatment purposes, the compounds defined by formula I, IA, II, IIA, III and IIIA are formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds are administered orally, topically, parenterally, nasally, rectally, sublingually or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 µg to about 1 mg per day of the compound are appropriate for treatment purposes. In some such embodiments an appropriate and effective dose may range from 0.01 µg to 1 mg per day of the compound. In other such embodiments an appropriate and effective dose may range from 0.1 µg to 500 µg per day of the compound. Such doses will be adjusted according to the type of disease or condition to be treated, the severity of the disease or condition, and the response of the subject as is well understood in the art. The compound is suitably administered alone, or together with another active vitamin D compound.

In one embodiment, the compound of formula IA is used in a pharmaceutical composition. For example, each ml of the pharmaceutical composition may comprise 51 g of the compound, 30% (v/v) propylene glycol and 20% (v/v) alcohol.

Compositions for use in the invention include an effective amount of (20R)-2-methylene-19,26,27-trinor-1α,25-dihydroxycalciferol (RA-7), (20R)-2α-methyl-19,26,27-trinor-1α,25-dihydroxycalciferol and (20R)-2β-methyl-19,26,27-trinor-1α,25-dihydroxycalciferol as the active ingredient, and a suitable carrier. An effective amount of the compound for use in accordance with some embodiments of the invention will generally be a dosage amount such as those described herein, and is administered topically, transdermally, orally, nasally, rectally, sublingually or parenterally. In one embodiment, the dosage is administered intraperitoneally.

The compounds of formula I, IA, II, IIA, III or IIIA are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The compound is formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration is in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration are in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and is prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

We claim:

1. A compound having the formula I:

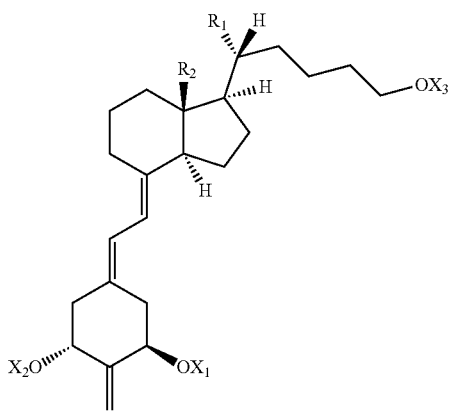

wherein $X_1$, $X_2$ and $X_3$ are independently selected from H and hydroxy protecting groups and $R_1$ and $R_2$ are independently selected from H or straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms.

2. The compound of claim 1, wherein $X_1$, $X_2$ and $X_3$ are hydroxy protecting groups.

3. The compound of claim 2, wherein $X_1$, $X_2$ and $X_3$ are triethylsilyl or t-butyldimethylsilyl groups.

4. A pharmaceutical composition, comprising an effective amount of the compound of claim 1 and a pharmaceutically acceptable carrier.

5. The pharmaceutical composition of claim 4 wherein the effective amount comprises from about 0.01 µg to about 1 mg of the compound per gram of the composition.

6. The pharmaceutical composition of claim 4 wherein the effective amount comprises from about 0.1 µg to about 500 µg of the compound per gram of the composition.

7. A method of treating a subject suffering from a biological condition, comprising administering an effective amount of the compound of claim 1 to the subject, wherein the biological condition is selected from psoriasis; leukemia; colon cancer; breast cancer; prostate cancer; skin cancer; lung cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; osteopenia; or osteoporosis.

8. The method of claim 7, wherein the biological condition is renal osteodystrophy, vitamin D-resistant rickets, osteoporosis or psoriatic arthritis.

9. The method of claim 7, wherein the biological condition is selected from leukemia, colon cancer, breast cancer, skin cancer, lung cancer or prostate cancer.

10. The method of claim 7, wherein the biological condition is selected from multiple sclerosis, lupus, diabetes mellitus, host versus graft reaction, or rejection of organ transplants.

11. The method of claim 7, wherein the biological condition is selected from rheumatoid arthritis, asthma, or inflammatory bowel diseases selected from celiac disease, ulcerative colitis and Crohn's disease.

12. The method of claim 7, wherein the biological condition is selected from wrinkles, lack of adequate skin firmness, lack of adequate dermal hydration, or insufficient sebum secretion.

13. The method of claim 7, wherein the compound is administered orally, parenterally, transdermally, nasally, rectally, sublingually or topically to the subject.

14. The method of claim 7, wherein the compound is administered intraperitoneally.

15. The method of claim 7, wherein the compound is administered in a dosage of from 0.01 µg per day to 1 mg per day.

16. A compound having the formula IA:

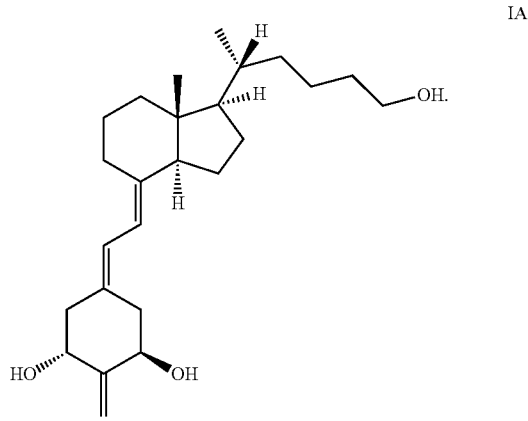 [SMILES: C=C1[C@H](O)CC(=C/C=C2\CCC[C@]3(C)[C@@H]([C@H](C)CCCCO)CC[C@@H]23)C[C@H]1O]

17. A pharmaceutical composition, comprising an effective amount of the compound of claim 16 and a pharmaceutically acceptable carrier.

18. The pharmaceutical composition of claim 17, wherein the effective amount comprises from about 0.01 µg to about 1 mg of the compound per gram of the composition.

19. The pharmaceutical composition of claim 17, wherein the effective amount comprises from about 0.1 μg to about 500 μg of the compound per gram of the composition.

20. A method of treating obesity of an animal, inhibiting adipocyte differentiation, inhibiting SCD-1 gene transcription, and/or reducing body fat in an animal comprising administering to an animal in need thereof an effective amount of a compound having the formula I:

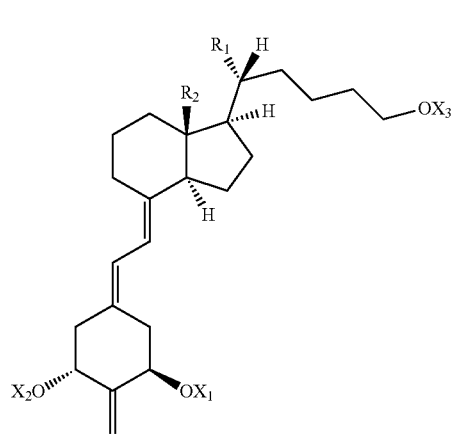

wherein $X_1$, $X_2$ and $X_3$ are independently selected from H and hydroxy protecting groups and $R_1$ and $R_2$ are independently selected from H or straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms.

21. The method of claim 20, wherein the compound is administered orally, parenterally, nasally, rectally, sublingually, transdermally or topically to the animal.

22. The method of claim 20, wherein the compound is administered in a dosage of from 0.01 μg per day to 1 mg per day.

23. The method of claim 20, wherein the compound is 2-methylene-1α,25-dihydroxy-19,26,27-trinorvitamin $D_3$ having the formula:

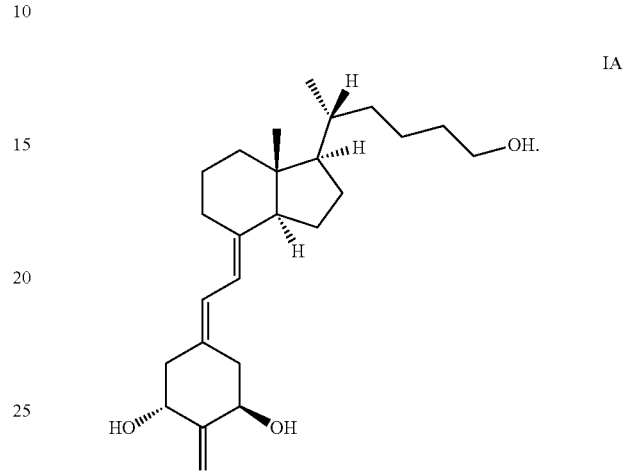

24. The method of claim 20, wherein the animal is a human.

25. The method of claim 20, wherein the animal is a domestic animal.

26. The method of claim 20, wherein the animal is an agricultural animal.

* * * * *